(12) United States Patent
Imai et al.

(10) Patent No.: US 8,395,766 B2
(45) Date of Patent: Mar. 12, 2013

(54) FOREIGN MATTER INSPECTION APPARATUS

(75) Inventors: Eiji Imai, Hitachinaka (JP); Masami Ooyama, Hitachi (JP); Hideyuki Okamoto, Hitachinaka (JP); Hiroyuki Yamashita, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/009,366

(22) Filed: Jan. 19, 2011

(65) Prior Publication Data

US 2011/0109901 A1    May 12, 2011

Related U.S. Application Data

(63) Continuation of application No. 12/003,123, filed on Dec. 20, 2007, now Pat. No. 7,898,653.

(30) Foreign Application Priority Data

Dec. 20, 2006  (JP) ................................. 2006-342409
Dec. 27, 2006  (JP) ................................. 2006-350814

(51) Int. Cl.
  *G01N 21/00*  (2006.01)
(52) U.S. Cl. ................ 356/237.3; 356/237.1; 356/237.2
(58) Field of Classification Search .... 356/237.1–237.5, 356/392–394; 250/548, 559.41; 382/149, 382/154, 218, 261
  See application file for complete search history.

(56) References Cited

U.S. PATENT DOCUMENTS

| | | | |
|---|---|---|---|
| 4,586,822 A | 5/1986 | Tanimoto | |
| 4,908,656 A * | 3/1990 | Suwa et al. | 355/53 |
| 5,412,210 A * | 5/1995 | Todokoro et al. | 850/9 |
| 5,640,243 A | 6/1997 | Koitabashi et al. | |
| 6,031,607 A * | 2/2000 | Miyazaki | 356/237.1 |
| 6,278,957 B1 | 8/2001 | Yasuda et al. | |
| 6,476,388 B1 * | 11/2002 | Nakagaki et al. | 850/9 |
| 6,476,913 B1 | 11/2002 | Machida et al. | |
| 6,574,359 B1 * | 6/2003 | Hance | 382/149 |
| 6,693,713 B1 * | 2/2004 | Nakajima | 356/400 |
| 6,724,464 B2 * | 4/2004 | Yang et al. | 355/55 |
| 6,803,592 B2 * | 10/2004 | Yoshida | 250/548 |

(Continued)

FOREIGN PATENT DOCUMENTS

JP    5-47901    2/1993
JP    10-106941    4/1998

(Continued)

OTHER PUBLICATIONS

Entire Prosecution of U.S. Appl. No. 12/003,123 to Imai, et al., filed Dec. 20, 2007, entitled "Foreign Matter Inspection Apparatus".

(Continued)

*Primary Examiner* — Sang Nguyen
(74) *Attorney, Agent, or Firm* — McDermott Will & Emery LLP

(57) ABSTRACT

Selection with alignment marks of an optimal template, its identification and similarity judgment are conducted by a calculation function of a correlation value provided to a foreign matter inspection apparatus. In other words, the foreign matter inspection apparatus includes unit for registering feature points of alignment marks formed on a surface of an inspected object, unit for collecting image data of the alignment marks formed on the surface of the inspected object and a data processor for extracting a feature point from the image data and calculating a correlation value of both feature points, and registers the image data of the alignment mark on the basis of a threshold value of the correlation value.

22 Claims, 17 Drawing Sheets

U.S. PATENT DOCUMENTS

| | | | |
|---|---|---|---|
| 6,850,320 | B2 | 2/2005 | Shibata et al. |
| 6,855,929 | B2 * | 2/2005 | Kimba et al. .................... 850/9 |
| 6,883,160 | B2 | 4/2005 | Tsuchiya et al. |
| 6,897,938 | B2 * | 5/2005 | Tanaka et al. ................... 355/53 |
| 6,992,766 | B2 * | 1/2006 | Tanaka et al. .................. 356/401 |
| 7,039,236 | B2 * | 5/2006 | Hashimoto et al. ........... 382/218 |
| 7,170,603 | B2 | 1/2007 | Katayama |
| 7,235,782 | B2 | 6/2007 | Takane et al. |
| 7,260,256 | B2 * | 8/2007 | Hiroi et al. .................... 382/141 |
| 7,302,672 | B2 * | 11/2007 | Pack et al. ......................... 430/5 |
| 7,332,359 | B2 | 2/2008 | Hamamatsu et al. |
| 7,349,575 | B2 | 3/2008 | Hattori et al. |
| 7,365,322 | B2 * | 4/2008 | Miyamoto et al. ............ 250/310 |
| 7,838,858 | B2 * | 11/2010 | Okita ........................ 250/559.44 |
| 2002/0036777 | A1 * | 3/2002 | Tanaka .......................... 356/401 |
| 2006/0017927 | A1 * | 1/2006 | Kim et al. ..................... 356/401 |
| 2006/0126916 | A1 | 6/2006 | Kokumai |

FOREIGN PATENT DOCUMENTS

| | | |
|---|---|---|
| JP | 11-220006 | 8/1999 |
| JP | 11-340115 | 12/1999 |
| JP | 2000-161932 A | 6/2000 |
| JP | 2002-328015 A | 11/2002 |
| JP | 2003-035680 A | 2/2003 |
| WO | WO-2005/008753 A1 | 1/2005 |

OTHER PUBLICATIONS

Japanese Office Action, w/ English translation thereof, issued in Japanese Patent Application No. 2009-214167, dated Feb. 21, 2012.
Japanese Office Action, w/ English translation thereof, issued in Japanese Patent Application No. 2006-342409, dated Feb. 21, 2012.
Japanese Office Action, and English translation thereof, issued in Japanese Patent Application No. 2009-214167 dated Sep. 25, 2012.

* cited by examiner

| ORDER | TEMPLATE CANDIDATE | SCORE VALUE | ACQUIRED IMAGE | COORDI-NATES (X,Y) | JUDGMENT | ANGLE CORRECTION VALUE | SIZE CORRECTION VALUE |
|---|---|---|---|---|---|---|---|
| No.1 | | XX | ACQUIRED IMAGE 1 | (X1,Y1) | OK | θ1 | 118% |
| No.2 | | YY | ACQUIRED IMAGE 2 | (X2,Y2) | OK | θ2 | 98% |
| No.3 | | ZZ | ACQUIRED IMAGE 3 | (X3,Y3) | NG | θ3 | 105% |

FOREIGN MATTER INSPECTION APPARATUS

RELATED APPLICATIONS

This application is a Continuation of U.S. patent application Ser. No. 12/003,123, filed on Dec. 20, 2007, now U.S. Pat. No. 7,898,653 claiming priority from Japanese Patent Application Nos. 2006-342409, filed on Dec. 20, 2006 and 2006-350814, filed on Dec. 27, 2006, the entire contents of each of which are hereby incorporated by reference.

BACKGROUND OF THE INVENTION

This invention relates to a foreign matter inspection apparatus for detecting foreign matters, scratches, defects, contamination, and so forth (which will be altogether referred to as "foreign matters") existing on a surface of an inspected object such as a glass substrate, a semiconductor wafer, or the like. More particularly, the invention relates to a foreign matter inspection apparatus for highly precisely correcting a position of an inspected object and detecting foreign matters with high accuracy and high sensitivity.

An apparatus for detecting the existence of foreign matters existing on a surface of an inspected object such as a glass substrate and a semiconductor wafer by irradiating an optical beam such as a laser beam to the surface of the inspected object and detecting a reflected or scattered beam occurring from the surface is known as a foreign matter inspection apparatus for (refer to JP-A-5-47901). In this foreign matter inspection apparatus, an image signal is generated from the intensity of reflected or scattered beams detected from each chip when a large number of IC chips originally having the same pattern are formed on a semiconductor wafer, and this image signal is compared with an image signal obtained from an adjacent chip or with an image signal from an approved chip prepared in advance. A matter on the surface of the semiconductor wafer is judged as the foreign matter when a difference between these image signals is greater than a threshold value.

When the image signal described above is collected, chips juxtaposed in a transverse direction on the surface of the inspection object must be put in parallel with a scanning direction of the optical beam. Because the difference signal is collected through comparison with the adjacent chips, variance occurs in the difference signal owing to the kind of the pattern contained in the detection region or the difference of the density such as wiring layout inside the chips and scribe lines among the chips and the inspection result is adversely affected.

As an alignment method for arranging parallel the inspected object, a method has been employed that collects coordinates (X, Y) of two points inside the inspected object with alignment marks formed inside the chips on the surface of the inspected object as the reference, and moves an inspection stage for correction on the basis of the deviation amount of the inspected object calculated from the coordinates.

Detection of foreign matters having smaller sizes has become necessary in recent years with the increase of an integration density and further miniaturization of semiconductors. To suppress variance of the error signal and to improve detection accuracy and reproducibility, higher alignment accuracy has been required. Nonetheless, alignment has become more and more difficult owing to miniaturization of the alignment marks and the drop of contrast resulting from the manufacturing process.

A method that prepares a projection waveform of a reticle substrate as reference image data (hereinafter called "template") and determines an error amount from pattern matching with a projection waveform obtained in practice from a position adjustment rectile substrate is known as an alignment method of an inspection position (refer to JP-A-10-106941, for example).

As for pattern matching methods, a method that detects an image signal from an inspection object, extracts a predetermined feature amount from the image signal to form an abstracted pattern and executes pattern matching between this abstracted pattern and an abstracted pattern obtained from the reference image (template) is known (refer to JP-A-11-340115, for example).

When a position error of a pattern wafer put on a movable stage is automatically aligned in an inspection apparatus for inspecting a pattern wafer, chips are aligned accurately and precisely on the pattern wafer. To inspect the pattern wafers, the wafers must be aligned in X and Y directions of a stage. However, immediately after the wafers are transferred to the stage, the wafers are not correctly aligned in the X and Y directions and must be positioned in the X and Y directions by rotating the stage.

To align the pattern wafers, a plurality of correction marks is formed, a CCD camera is used to image the positions of the correction marks and these positions are measured by a pattern matching process. A rotation angle of the stage to be corrected is then calculated from a plurality of points.

Generally, imaging is made in alignment by using two kinds of magnification cameras. To improve accuracy of the correction angle to be calculated, the positions of the correction marks must be detected with high accuracy. However, the imaging visual field of the magnification camera is narrow and the probability of covering the correction marks by a single imaging operation becomes low. For this reason, a system has been employed that detects a rough position by a low magnification camera and then accuracy is improved by switching the camera to a high magnification camera.

However, this system involves the problem that alignment needs a long time. To improve inspection through-put, it would be conceivable to derive an optimal magnification ratio from alignment accuracy and a positioning error of the stage at the time of transfer and to conduct alignment at a single magnification. JP-A-11-220006 can be cited as one of the references relating to this technology.

In alignment at a single magnification, however, three or more marks of correction marks for calculating a correction angle for detecting a recognition error of other pattern as a correction mark and confirmation marks for confirming alignment accuracy are necessary. When the wafer is transferred to the stage, the center of the wafer deviates from the center of the stage and the coordinate position of the correction mark for confirmation deviates, too. Therefore, the coordinate position of the confirmation mark must be detected before correction. However, the movement of the stage and the pattern matching processing become necessary and the processing time gets elongated. The coordinates of the confirmation mark must be therefore calculated in advance from the coordinates of the correction mark detected.

The technology described in JP-A-10-106941 executes a collective correction processing of a position error amount between going and returning strokes when an inspected object is scanned in going and returning directions by optical beams. This technology cannot be applied to a foreign matter inspection apparatus that requires high precision alignment of individual inspected objects. Since the technology is directed to a reticle substrate produced as a jig that is dedicated to the adjustment of the positioning error, it does not take into consideration those adverse influences which may be exerted on various kinds of thin films produced in the manufacturing process of semiconductor devices such as semiconductor films, metal films, insulating films, and so forth, and problems of the recognition failure due to the drop of contrast of the alignment marks and the matching mistake with other alignment marks are unavoidable.

It has been customary in the past for an operator to select an alignment mark while watching an observation screen of an inspected object and to register the image data as a template. When an inspection process of semiconductor device products is a manufacturing process which invites the drop of contrast, however, it is difficult to observe the alignment marks with eye. Therefore, the operator empirically repeats selection of the alignment marks but a long time is necessary to set a complicated evaluation condition of the template and a collection work. Furthermore, when an error of an angle (θ) occurs in the inspected object, it is difficult to use the template as such and correction of the angle is necessary. The error of the correction process results in the drop and variance of alignment accuracy.

SUMMARY OF THE INVENTION

It is an object of the invention to conduct pattern matching in such a fashion as not to invite recognition failure and recognition mistake even when alignment marks of an inspected object are under a difficult condition for conducting pattern matching.

It is another object of the invention to make it easy to select a suitable template and to set an evaluation condition by providing functions of analyzing whether or not an image of a pattern collected from an inspection object is suitable as a template and registering the result.

It is still another object of the invention to improve inspection through-put of an inspection apparatus.

In a foreign matter inspection apparatus for inspecting the existence of foreign matters on a surface of an inspected object by irradiating optical beams to the surface of the inspected object, acquiring an image signal from a reception intensity of reflected or scattered beams and comparing the image signal with an image signal acquired from an adjacent inspected object, the foreign matter inspection apparatus according to the invention comprises a device for registering feature points of alignment marks formed on the surface of the inspected object; and a device for reading the alignment marks on the surface of the inspected object; wherein alignment is executed by detecting the alignment marks formed on the surface of the inspected object on the basis of the feature points.

In a foreign matter inspection apparatus for inspecting the existence of foreign matters on a surface of an inspected object from a reception intensity of reflected or scattered beams from the inspected object by irradiating optical beams to the surface of the inspected object, the foreign matter inspection apparatus according to the invention comprises a device for inputting feature points of alignment marks formed on the surface of the inspected object; a device for displaying the feature points of the alignment marks inputted; and a device for registering feature points of the alignment marks inputted; wherein alignment is conducted by detecting the alignment marks formed on the surface of the inspected object on the basis of the feature points.

In a foreign matter inspection apparatus for inspecting the existence of foreign matters on a surface of an inspected object from a reception intensity of reflected or scattered beams by irradiating optical beams to the surface of the inspected object, the foreign matter inspection apparatus according to the invention comprises a device for registering feature points of alignment marks formed on the surface of the inspected object; a device for collecting image data of the alignment marks formed on the surface of the inspected object; and a data processor for extracting feature points from the image data and calculating a correlation value from both of the feature points; wherein the image data of the alignment marks are registered on the basis of a threshold value of the correlation value.

In a foreign matter inspection apparatus for inspecting the existence of foreign matters on a surface of an inspected object from a reception intensity of reflected or scattered beams by irradiating optical beams to the inspected object, the foreign matter inspection apparatus according to the invention comprises a device for registering feature points of alignment marks formed on the surface of the inspected object; a device for collecting image data of the alignment marks formed on the surface of the inspected object; a data processor for extracting feature points from the image data and calculating a correlation value from both of the feature points; and a display device for displaying a calculation result of the correlation value; wherein a judgment result of approval/rejection of the alignment marks is displayed on the basis of a threshold value of the correlation value. It is preferred in this foreign matter inspection apparatus that the calculation result of the correlation value is arranged in the order of the size of the correlation values and is displayed in a list form on the display apparatus described above.

In a foreign matter inspection apparatus for inspecting the existence of foreign matters on a surface of an inspected object by irradiating optical beams to the surface of the inspected object, acquiring an image signal from a reception intensity of reflected or scattered beams and comparing the image signal with an image signal acquired from an adjacent inspected object, the foreign matter inspection apparatus according to the invention comprises image processing unit for extracting feature points of alignment marks formed on the surface of the inspected object and conducting pattern matching with feature points of a template; processing means for calculating a probability or score from both of the feature points subjected to pattern matching; judgment processing unit for identifying an alignment mark as a reference when the feature points are coincident with one another with a predetermined probability or score; another processing unit for calculating a difference amount of the inspected object from coordinates collected by recognition of at least two alignment marks inside the inspected object; and a driving mechanism for conducting alignment by moving an inspection stage on the basis of the difference amount.

To automatically select an optimal alignment mark or marks in the invention, the foreign matter inspection apparatus according to the invention may be provided with an evaluation function of the alignment marks as to whether or not the image data is suitable as a template, a display function of displaying the evaluation result, a selection function of the alignment marks and a registration function of storing the image data as the template.

To automatically extract the alignment mark as a template candidate, the foreign matter inspection apparatus may further include data input means for inputting the feature points of the template, data registration means for storing data, detection means for collecting the image data of a designated zone inside a chip on the basis of the feature points of the template, data registration means for storing the image data collected, image processing means for extracting the feature points from the image data, a data processing unit for comparing the feature points of the template stored, display means for displaying coordinates of the alignment mark collected and its appearance, and analytical values calculated by the data processing unit such as suitability number and suitability rank, and registration means for registering image data by automatically selecting the alignment mark as an optimal template from among the alignment marks.

To evaluate in advance the possibility of the recognition error of the template candidate, the foreign matter inspection apparatus may further comprises detection unit for collecting image data of a designated zone inside a chip on the basis of the feature points of the template candidate extracted, data registration unit for storing the image data collected, image processing means for extracting the feature points from the image data, a data processing unit for comparing the feature points of the template stored, and display unit for displaying coordinates of the image data collected and its appearance and analytical values calculated by the data processing unit such as suitability number and suitability rank.

One of the features of the invention for accomplishing the objects described above resides in a foreign matter inspection apparatus which comprises unit for detecting coordinates of marks of two points for correction, unit for calculating a correction angle of a wafer from the coordinates of the correction marks of the two points, unit for calculating the coordinates of a mark for confirmation from the correction angle of the wafer, the coordinates of the correction mark and coordinates of confirmation mark registered in advance when the wafer is transferred to a stage, unit for calculating the coordinates of the confirmation mark when the stage is rotated by the correction angle, unit for detecting the coordinates of the confirmation mark, and unit for comparing the coordinates of the confirmation mark detected with the coordinates of the confirmation mark calculated when the stage is rotated. This and other features of the invention will become more apparent from the following description.

According to the invention, pattern matching can be executed while recognition failure and recognition error of the alignment marks are suppressed.

According to the invention, inspection through-put of the inspection apparatus can be improved. When alignment is made, for example, an inclination of the wafer is calculated from coordinates of two points and correction accuracy must be confirmed after the correction is made. Detection of the coordinates of the two points for confirmation is time consuming and the time can be shortened by detecting the coordinates of one other point. However, the center of the stage deviates from the center of the wafer after transfer of the wafer and the positions of the confirmation marks are also deviated, and a detection of the confirmation marks is required. When the positions of the confirmation marks are calculated by taking the deviation of the center between the stage and the wafer into account, alignment can be conducted without the necessity for detecting the confirmation marks before correction.

Other objects, features and advantages of the invention will become apparent from the following description of the embodiments of the invention taken in conjunction with the accompanying drawings.

DESCRIPTION OF THE INVENTION

Embodiments of the invention will be hereinafter explained in detail with reference to the accompanying drawings. A foreign matter inspection apparatus according to the invention can inspect those foreign matters which exist on a surface of an inspected object such as a semiconductor wafer, an ALTIC substrate and a glass substrate used for TFT-LCD, but the following explanation will be directed to the semiconductor wafer as an example of the inspected object.

An embodiment of the invention that improves a processing speed of alignment and detects recognition error of marks by using two correction marks and one confirmation mark will be explained.

Embodiment 1

Figure 1:
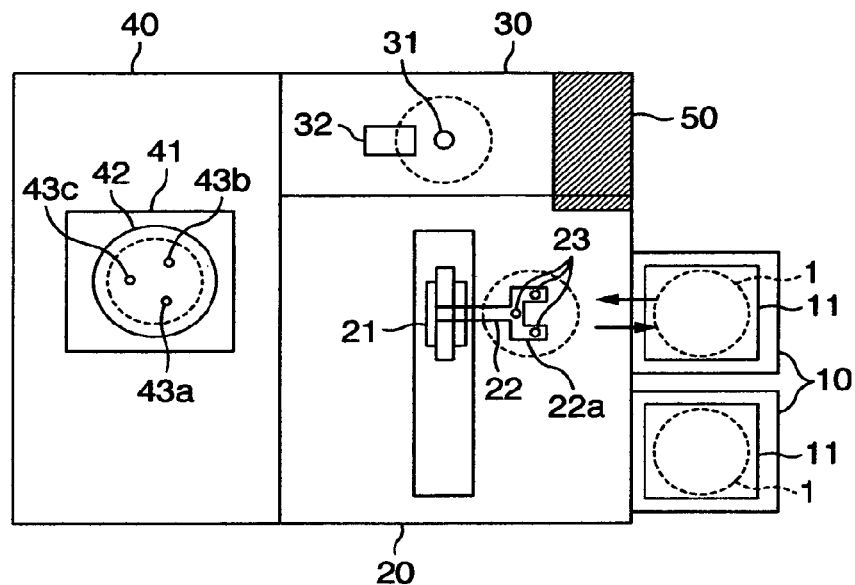
FIG. 1 is a plan view showing a rough construction of a foreign matter inspection apparatus according to the invention.

FIG. 1 is a plan view showing a rough construction of a foreign matter inspection apparatus according to an embodiment of the invention. The foreign matter inspection apparatus includes one or more load ports 10, a transfer unit 20, a pre-alignment unit 30, an inspection unit 40 and a data processing unit 50. One ore more wafer cassettes 11 accommodating a plurality of semiconductor wafers 1 to be inspected is put on the load ports 10. The wafer cassettes 11 may be divided into those for transferring the semiconductor wafers 1 to be inspected and those for recovering the semiconductor wafers 1 that are judged as defective as a result of inspection.

Figure 2:
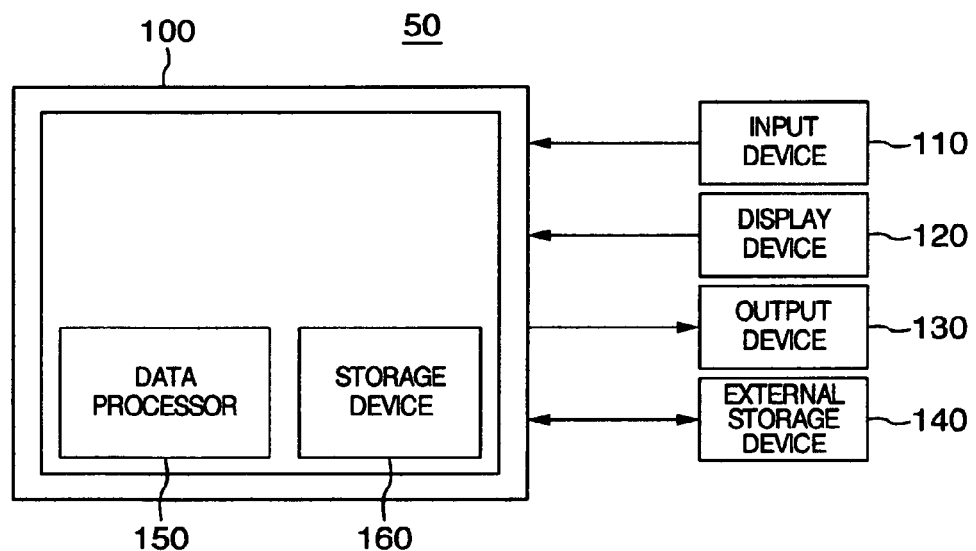
FIG. 2 is a block view showing an outline of control of a data processing unit.

FIG. 2 is a block view showing an outline of control of the data processing unit 50. The data processing unit 50 includes a host computer 100, an input device 110 such as a keyboard, a touch panel or a mouse, a display device 120 such as a CRT or a flat panel display, an output device 130 such as a printer and an external storage device 140 for controlling external media such as a floppy (registered trade mark) disk (FD) or a compact disk (CD). The host computer 100 has a data processor 150 and a storage device 160 such as a hard disk drive (HDD). The host computer 100 controls the entire foreign inspection apparatus on the basis of the instruction from the input device 110. The display device 120 displays control relating to alignment, the result of analysis, control of the inspection condition, analysis of data collected and the operating condition of the foreign matter inspection apparatus and furthermore, outputs these data to the output device 130 such as the printer. Setting of the various conditions is inputted through the input device 110 and is stored as recipe data in the storage device 160.

Figure 14:
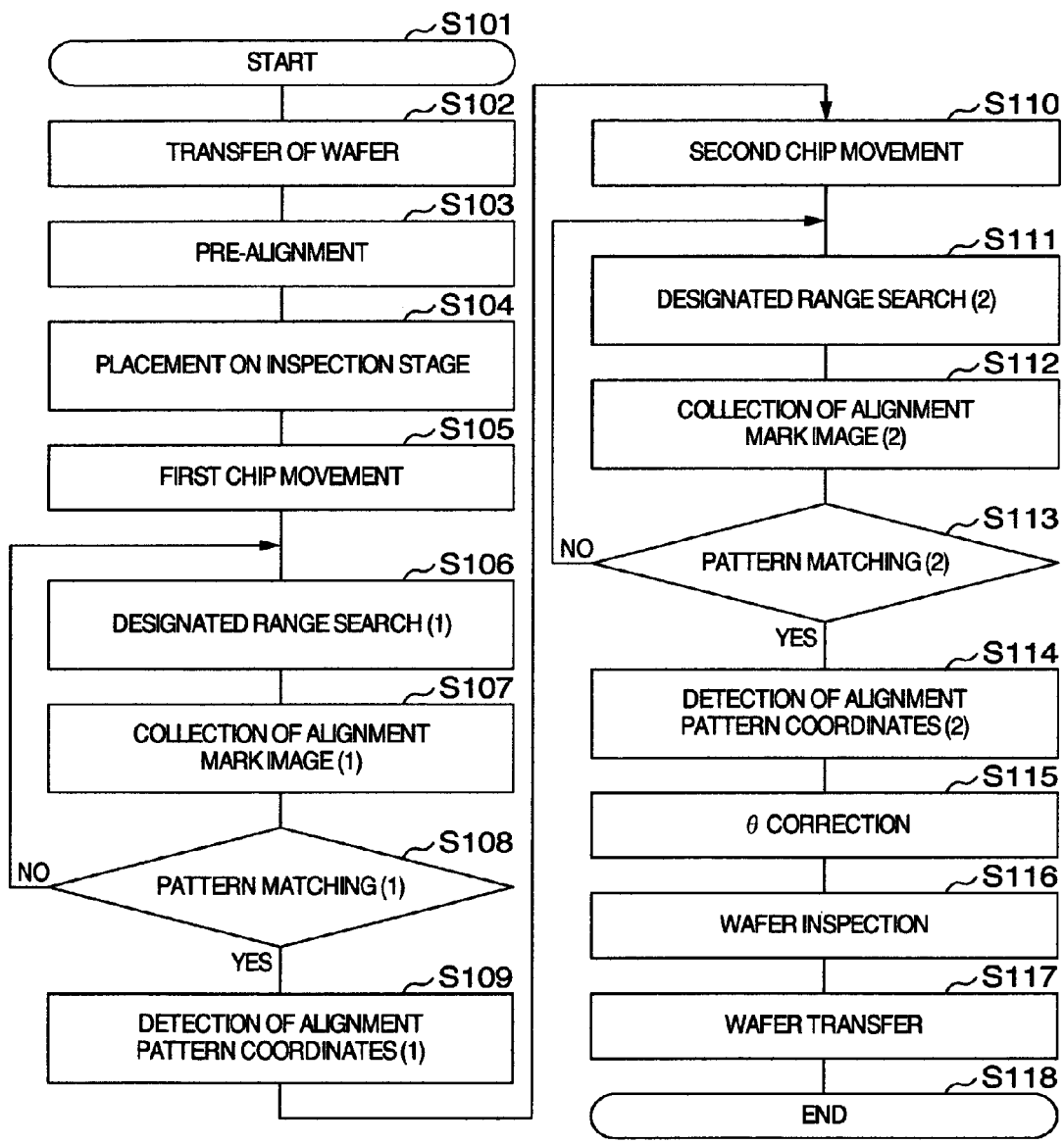
FIG. 14 is a flowchart that represents a method of angle correction of a semiconductor wafer by using a template.

FIG. 14 is a flowchart showing a processing procedure of the semiconductor wafer 1 in the first embodiment. In the foreign matter inspection apparatus shown in FIG. 1, transfer of the semiconductor wafer 1 is carried out as a signal is transmitted from the data processing unit 50 upon execution of a transfer program (S101), a servo motor is driven through a pulse control substrate and a driving circuit, not shown, and a handling arm 22 provided to a transfer assembly 21 is controlled. The handling arm 22 takes out the semiconductor wafer 1 from the rack of the wafer cassette 11 designated by the data processing unit 50 and transfers it to the pre-alignment unit 30 from the load port 10 (S102). When the semiconductor cassette 1 is taken out from the wafer cassette 11, the wafer cassette 11 is controlled in such a fashion that a substantial center of a U-shaped contact portion 22*a* is in conformity with a substantial center of the semiconductor wafer 1 and the semiconductor wafer 1 is vacuum adsorbed to and held by an adsorption opening 23 of the contact portion 22*a*.

The handling arm 22 moves forward above the pre-alignment chuck 31 while holding the semiconductor wafer 1, descends at the position at which the substantial center of the semiconductor wafer 1 is coincident with that of the pre-alignment chuck 31 and mounts the semiconductor wafer 1 onto the pre-alignment chuck 31. Next, the pre-alignment chuck 31 vacuum adsorbs the back of the semiconductor wafer 1 and holds the semiconductor wafer 1.

The pre-alignment chuck 31 is so constituted as to be capable of moving and rotating in X, Y and θ directions. The detection device 32 has a light emission unit such as a laser beam, and a light reception unit such as a CCD line sensor, detects the position of light reaching the light reception unit from the light emission unit and its intensity and detects the outer circumference of the semiconductor wafer 1 and the position of a V notch (or so-called "orientation flat"). The data processing unit 50 drives the pulse motor through a pulse control circuit and a driving circuit, each not shown, on the basis of the detection result of the detection device 32 and moves and rotates the pre-alignment chuck 31 to thereby execute rough position adjustment (pre-alignment) of the semiconductor wafer 1 (S103).

After pre-alignment is completed, the pre-alignment chuck 31 releases vacuum adsorption of the semiconductor wafer 1. The handling arm 22 moves below the semiconductor wafer 1 that is mounted onto the pre-alignment chuck 31 and moves up at the position at which the center of the U-shaped contact portion 22*a* is substantially coincident with the center of the semiconductor wafer 1 and lifts up the semiconductor wafer 1 from the pre-alignment chuck 31. The semiconductor wafer 1 is then transferred from the pre-alignment unit 30 to the inspection unit 40 (S104).

An inspection stage chuck 42 is provided to the inspection stage 41 in the inspection unit 40. The inspection stage chuck 42 has elevation pins 43*a*, 43*b* and 43*c* capable of moving up and down. The handling arm 22 moves forth above the inspection stage chuck 42 while lifting up the semiconductor wafer 1 under the state where the elevation pins 43*a*, 43*b* and 43*c* are elevated, moves down at the position at which the substantial center of the semiconductor wafer 1 is coincident with that of the inspection stage chuck 42 and delivers the semiconductor wafer 1 to the elevation pins 43*a*, 43*b* and 43*c*. Next, after the handling arm 22 moves back from the position above the inspection stage chuck 42, the elevation pins 43*a*, 43*b* and 43*c* are lowered and the semiconductor wafer 1 is mounted onto the inspection stage chuck 42. The inspection stage chuck 42 vacuum adsorbs the back of the semiconductor wafer 1 and fixes the semiconductor wafer 1.

Figure 3:
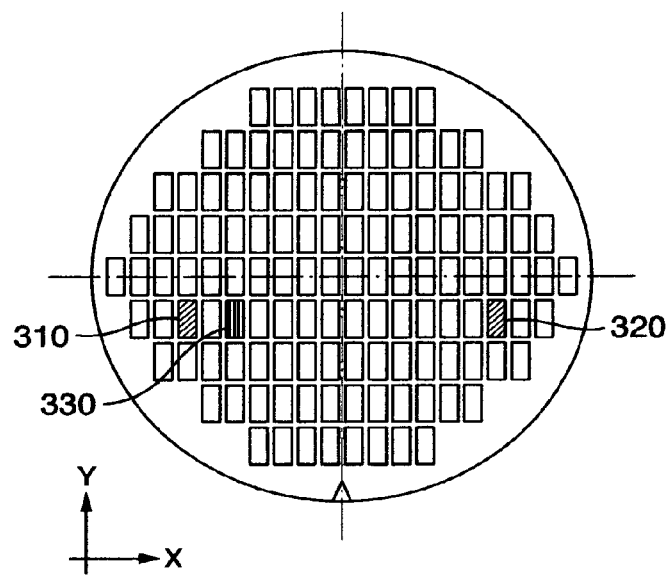
FIG. 3 is an explanatory view useful for explaining chips and designated coordinates used for alignment inside a semiconductor wafer.
Figure 3:
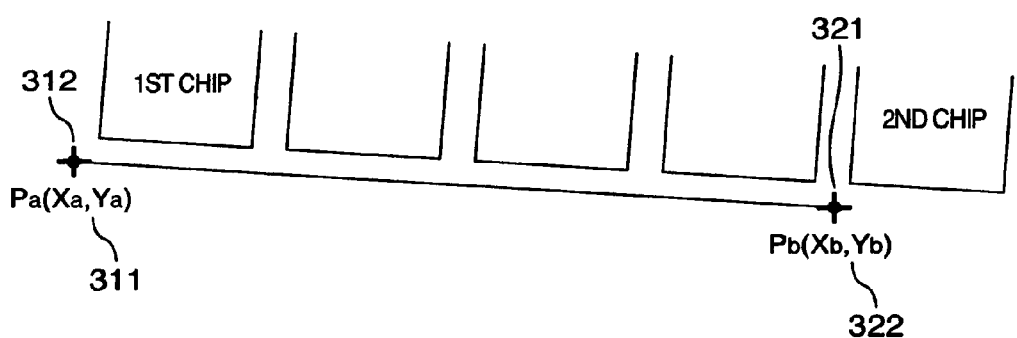

When the semiconductor wafer 1 is placed on the inspection stage chuck 42, the data processing unit 50 reads the chip size from the recipe data registered to the storage device 160 through the input device 110 and calculates the coordinates of the chips juxtaposed on the semiconductor wafer 1 by the data processor 150. The inspection stage chuck 42 is so constituted as to be capable of moving and rotating in the X, Y and directions and controls the inspection positions on the semiconductor 1, etc, while detecting the positions (coordinates) by a position detector (not shown in the drawing) such as a laser scale. The data processing unit 50 drives the servo motor (not shown in the drawing) through the pulse control substrate and the driving circuit, each not shown, and moves and rotates the inspection stage chuck 42 to move it to the first chip designated coordinates 311 of the first chip 310 shown in FIG. 3, for example (S105).

A CCD camera (not shown) is provided to an upper part of the inspection stage chuck 42 of the inspection unit 40. The CCD camera searches the designated range in the proximity of the first chip designated coordinates 311 (S106) and samples the first alignment mark 312 of the first chip 310 as image data, for example (S107). The data processor 150 calculates mean lightness of the entire image of the image data of the first alignment mark 312 so sampled on the basis of gradation data for each data. Next, a multiplier that makes this mean lightness substantially equal to mean lightness of a template is determined and the difference between lightness calculated by multiplying this multiplier for lightness of each pixel and the mean lightness of the entire image is calculated for each pixel. Owing to this normalization processing, the change between the pixels is extracted as normalized lightness waveforms (projection waveforms) and is stored in the storage device 160.

Though the lightness as the reference is the mean lightness of the template in this embodiment, a similar effect can be likewise obtained by determining a multiplier that adjusts lightness on the basis of set lightness that is in advance set.

Figure 4:
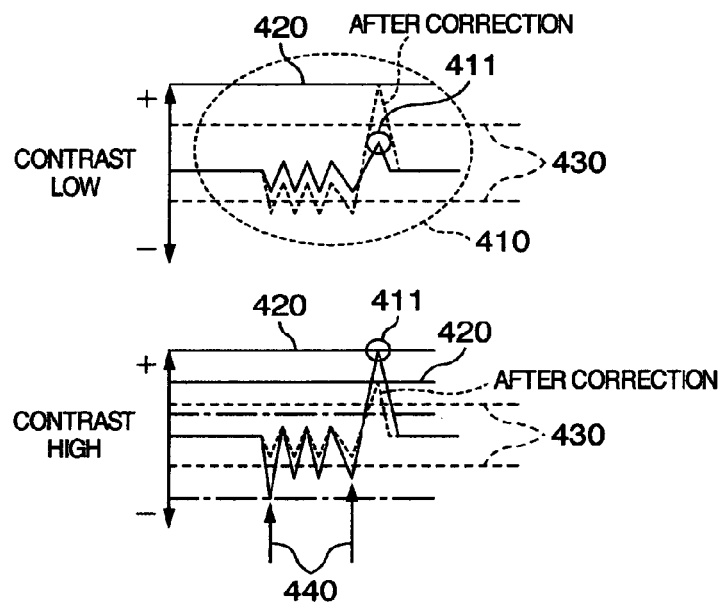
FIG. 4 is an explanatory view useful for explaining a processing of edge intensity waveform and edge positions.

The data processor 150 executes a calculation processing of the projection waveform and calculates an edge intensity waveform 410 representing the change of density (gradation) shown in FIG. 4 by differentiation, for example. Next, the data processor 150 extracts a maximum edge intensity value 411 representing a maximum value from the edge intensity waveform 410 so obtained, determines a multiplier that makes the maximum value substantially equal to a feature amount set value 420 set in advance and corrects the entire edge intensity waveform 410 on the basis of the multiplier so that the maximum edge intensity value 411 becomes high when contrast is low, and low when the contrast is high. This correction restricts influences of the drop of contrast such as the change of the film or illumination on the surface of the semiconductor wafer 1 on pattern matching accuracy.

An edge position 440 is detected from a peak exceeding a feature amount threshold value 430 registered in advance to the storage device 160 and the position of the pixel of the CCD on the basis of this threshold value 430 and stores the intensity value of each edge position 440 and the feature point such as the position of the pixel of the CCD in association with the positional information (coordinates information) from the position detector.

The image processing is executed for the data of the template as the reference of comparison in the same way as the first alignment mark 312 described above and the intensity value of each edge position 440 and the feature point such as the CCD pixel position are registered in advance to the storage device 160. Pattern matching of the first alignment mark 312 is made on the basis of the feature point of this template and comparison is judged (S108). When the first alignment mark 312 is different from the template pattern, for example, search inside the designated range is continued. Pattern matching is continued by repeating the steps S106 to S108 and an alignment mark providing correlation is searched. A pattern detected with a predetermined correlation is recognized as the first alignment mark 312 and the position detector detects the coordinates (X, Y) of the first alignment mark 312. The coordinates are then registered to the storage device 160 (S109). Because comparison judgment is made by using the feature points that are mutually normalized, high precision pattern matching can be secured even when the contrast of the first alignment mark 312 is low owing to the influences of the process steps and the recognition error can be suppressed.

The data processor 150 calculates an index value (score value) representing the matching state for the pattern recognized as the first alignment mark 312 by pattern matching on the basis of the feature point and displays it on the screen of the display device 120. The score value is calculated in accordance with equation (1), for example, on the basis of the correlation data of the feature point in the first alignment mark 312 and the template. The score value may be calculated by formulas other than equation (1) as long as they can express and display the degree of pattern matching, and similar effects can be acquired.

[Expression 1]

$$S = \sqrt{\frac{Mp}{Tt}} \times \sqrt{\frac{Mp}{Ta}} \times 10000 \quad (1)$$

Incidentally, symbol S in equation (1) represents the score value, Mp represents the number of coincidences of edges in pattern matching, Tt represents the total number of edges at the time of collection of the template and Ta represents the total number of edges of the first alignment mark 312.

The score value S is stored in the storage device 160 whenever pattern matching of the semiconductor wafer 1 is made and is displayed on the screen of the display device 120.

Whether or not the template is approved can also be judged, by confirming the pattern matching state through the score value S. The state of the alignment mark, that is to say, the manufacturing condition of semiconductor devices and the condition of the foreign matter inspection apparatus, can be diagnosed through comparison with the data of the past score values S. Display or warning of abnormality and apparatus abnormality can be transmitted to remote diagnosing means on the basis of the threshold value of the score value S that is set in advance, and they can be set through the input device 110 with selection of display/non-display of the score value S.

After the coordinates of the first alignment mark 312 are detected, the inspection stage chuck 42 is moved to the second chip designated coordinates 321 on the chip matrix of the semiconductor wafer 1 (S110). Image processing and pattern matching are executed for the second alignment mark 322 of the second chip 320 in the same way as the first alignment mark 312 (S111 to S113). The coordinates (X, Y) of the second alignment mark 322 are detected and are stored in the storage device 160 with the score value calculated (S114). A set value (threshold value) of a management reference value of this score value can be set from a setting window arranged on the screen of the display device 120. When at least one of the first alignment mark 312 and the second alignment mark 322 does not satisfy the condition of the threshold value, alarm display can be made through the data processing unit 50.

Incidentally, the calculation step in the data processing of the score value may be skipped, and the data processing method and the display method can be changed through setting from the input device 110, depending on the condition of the use of the foreign matter inspection apparatus such as when condition monitor of pattern matching is not necessary because the occurrence of the recognition error is less or when through-put of the foreign matter inspection apparatus is required.

The data processor 150 calculates the difference of the angle from the two (X, Y) coordinates of the first alignment mark 312 and the second alignment mark 322 and the angle of the inspection stage chuck 42 is corrected on the basis of the instruction from the data processing unit 50 (S115). The chips juxtaposed on the semiconductor wafer 1 are put highly precisely in parallel with the scanning direction of the optical beam.

A light projection system apparatus and a light reception system apparatus, each not shown, are arranged above the inspection stage chuck 42 and the optical beam such as a laser beam is irradiated to the surface of the semiconductor wafer 1 from the light projection system apparatus. The inspection stage chuck 42 is moved in the Y and X directions by driving the servo motor to scan the optical beams on the surface of the semiconductor wafer 1.

The light reception system apparatus detects reflecting light or scattered light generated from the surface of the semiconductor wafer 1 and the host computer 100 of the data processing unit 50 executes data processing on the basis of the detection result of the light reception system apparatus to detect foreign matters that exist on the surface of the semiconductor wafer 1 (S116).

After the foreign matter inspection of the surface of the semiconductor wafer 1 is completed, the semiconductor wafer 1 is transferred from the inspection unit 40 to the load port 10 in the reverse procedure to the transfer of the semiconductor wafer 1 to the inspection stage chuck 42 and is stored in the same rack of the same wafer cassette 11. Incidentally, when the number of foreign matters on the surface of the semiconductor wafer 1 exceeds a set value, the semiconductor waver 1 may be classified and transferred to the wafer cassette 11 of other load port 10. Classification and transfer of the semiconductor wafers 1 at the time of transfer can be set from the input device 110 of the display device 120 through the input device 110.

In this embodiment, correction is made by using the two (X,Y) coordinates but when three or more (X,Y) coordinates positioned in vertical and transverse directions are used, higher correction can be made through the correction time needs a longer time. In this embodiment, correction is made by the chips of the same row arranged in the transverse direction relative to the notch of the semiconductor wafer 1, the chip arrangement may be corrected to be parallel to the scanning direction of the optical beam. Similar performance can be thus acquired by correction by chip arrangement in a longitudinal direction or an oblique direction or by an arbitrary chip arrangement.

The greater the distance between the first chip 310 and the second chip 320 that are used for the position correction, the higher becomes accuracy of the angle correction. The alignment mark is likely to come off from the designated search range or the recognition error is likely to occur when predetermined accuracy cannot be obtained for the angle correction of the pre-alignment chuck 31. Therefore, designated coordinates of an intermediate correction chip 330 are interposed between the first chip 310 and the second chip 320 and fine adjustment of the positioning error between the first chip 310 and the second chip 320 can be made after rough position correction is made by using this intermediate correction chip 330. Selection of the use of the intermediate correction chip and setting of various conditions can be set to the set screen on the display device 120 through the input device 110. The alignment mark can be recognized stably even in those semiconductor wafers 1 which have large positioning errors by selection means of the positioning error correction method.

Figure 5:
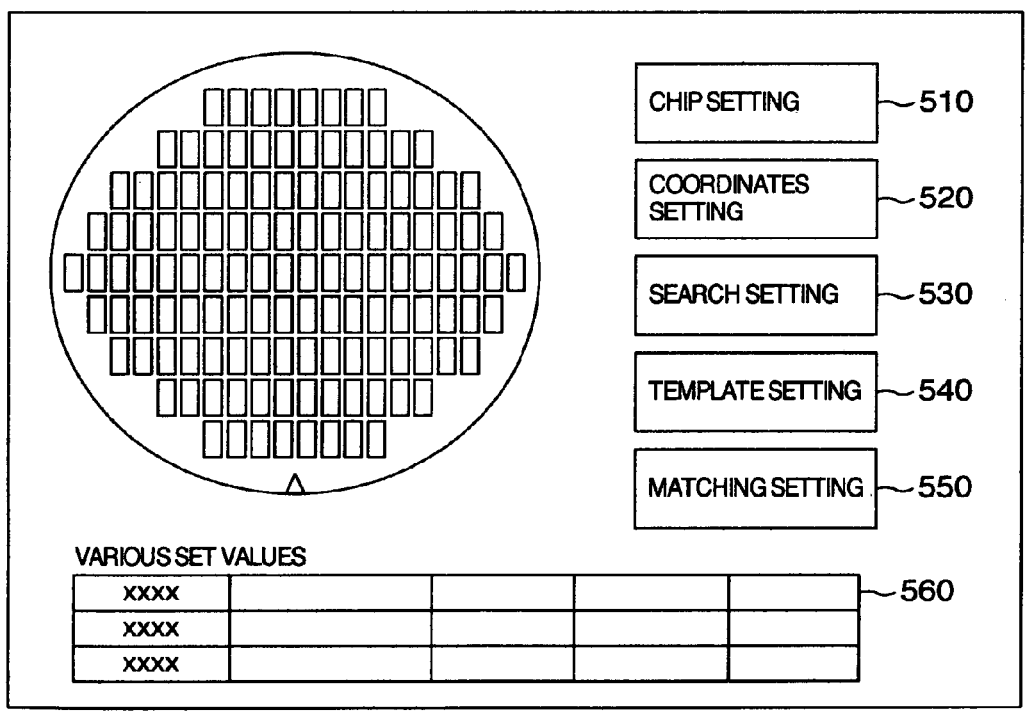
FIG. 5 is an explanatory view useful for explaining a set screen of alignment.

FIG. 5 shows the condition setting screen described above. The condition setting screen includes chip condition setting means 510 for setting the first chip 310, the second chip 320 and the intermediate correction chip 330, coordinate condition setting means 520 for setting the coordinates of the alignment marks such as the first chip designation coordinates 311, the second chip designated coordinates 321 and the intermediate correction chip designated coordinates, search condition setting means 530 for setting the range to be searched, template setting means 540 for setting the template used for pattern matching, and matching condition setting means 550 for setting the correction conditions such as the angle and the position, the data processing method of the score value and the threshold value. Setting of those conditions and numerical values which may govern matching among the set conditions of various items are displayed on the set value displaying means 560 at the top of the set screen. When each condition setting button is selected through the input device 110, the corresponding set screen is opened and each detailed data can be set. Though this embodiment uses buttons for the set screen, the set screen may be constituted by using icons, input spaces or other means as long as display and setting of the screen and the set condition can be made.

Embodiment 2

To discriminate the alignment marks by pattern matching, a template as a comparison object is necessary. Next, a method of collecting an optimal template from among the patterns formed on the semiconductor wafer 1 will be explained by mainly referring to FIGS. 6, 7 and 15. The explanation of those portions witch overlap with the first embodiment will be omitted and reference will be also made to FIGS. 1 and 2, whenever necessary.

Figure 6:
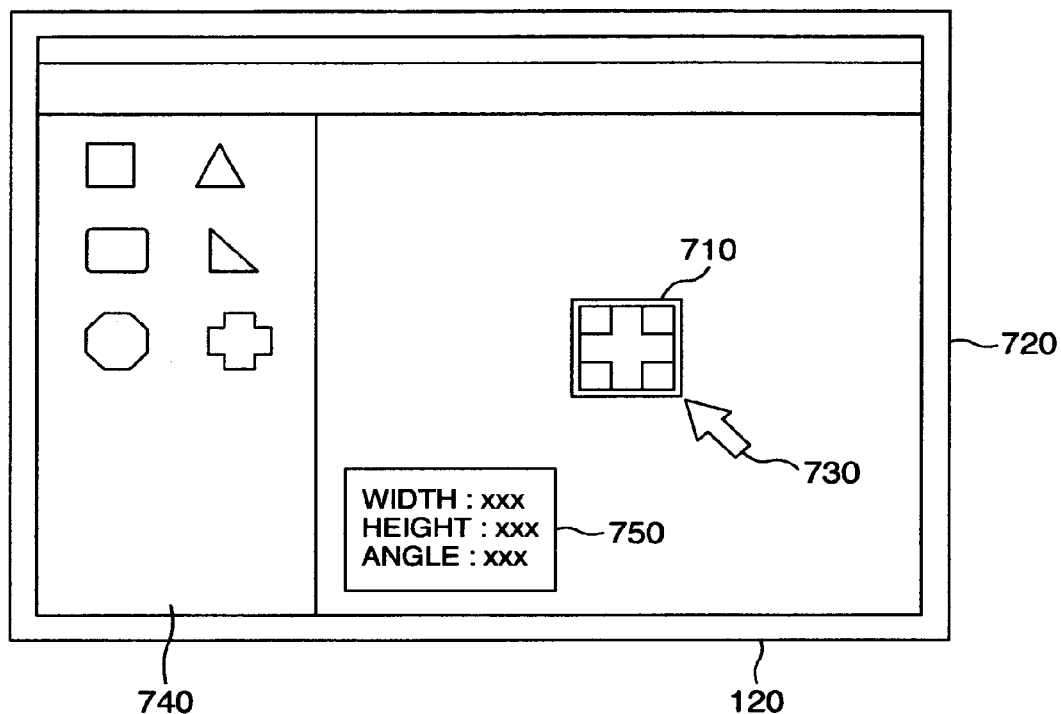
FIG. 6 is an explanatory view useful for explaining a CAD screen for plotting a template candidate.
Figure 15:
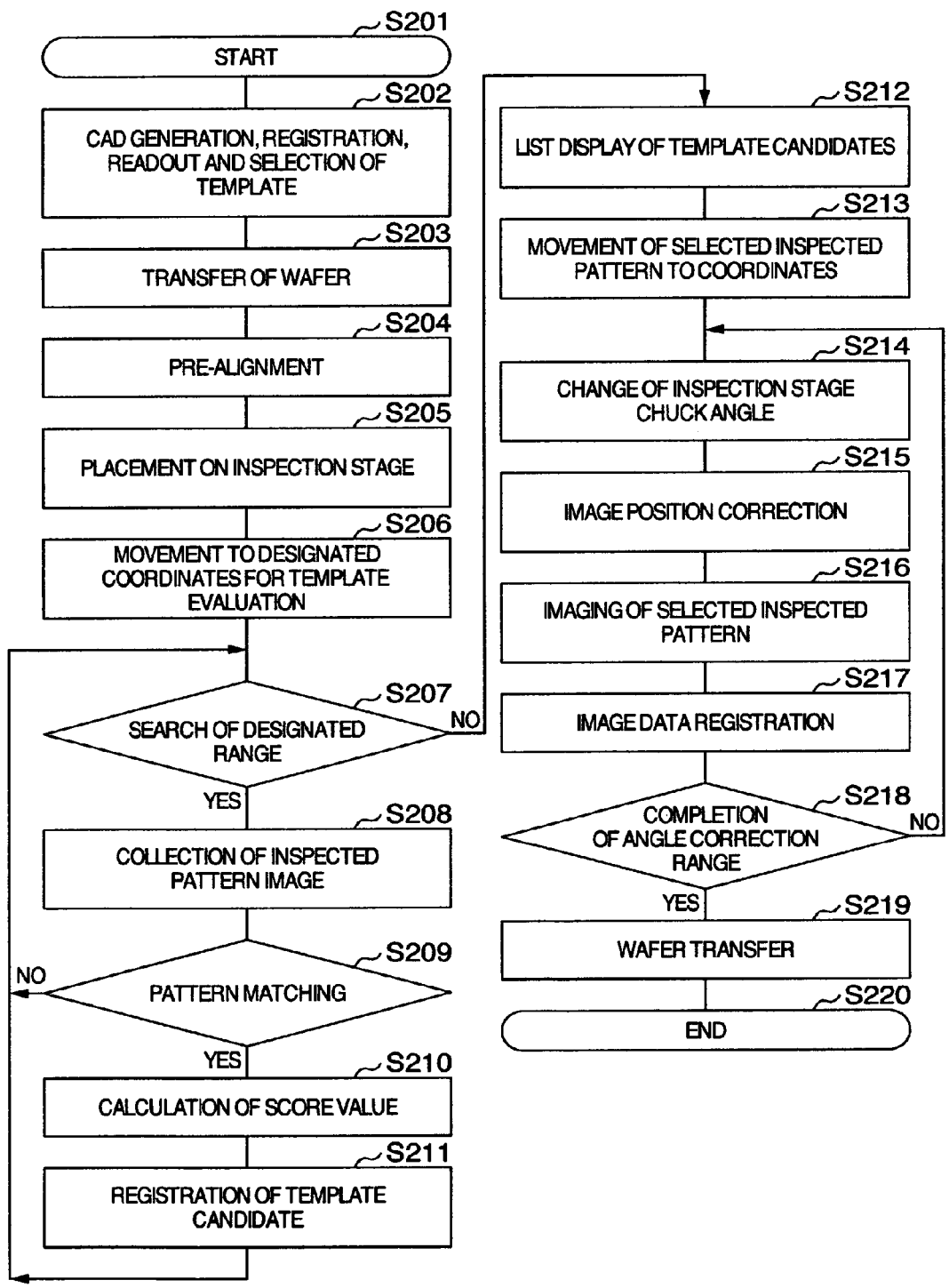
FIG. 15 is a flowchart that represents a method for collecting an optimal template.

FIG. 15 is a flowchart showing the processing procedure of the semiconductor wafer 1 in the second embodiment and FIG. 6 shows a CAD (Computer Aided Design) screen 720 for plotting a template candidate 710 of the alignment mark. The CAD screen 720 is provided as one of the functions of the foreign matter inspection apparatus and is displayed on the screen of the display device 120. The host computer 100 executes various processing for the CAD screen 720 on the basis of the instruction from the input device 110. A grid and a scale can be displayed on the CAD screen 720 and a rough size of the template candidate 710 can be confirmed. Shape information of the width, height and angle of the template candidate 710 can be displayed on appearance display means 720. Plotting means 740 for plotting and editing the template candidate 710 such as solid line, broken line, chain line, circle and rectangle, reversion and rotation of graphic, diminishing and enlargement of size, etc, is displayed on the CAD screen 720 by images such as icons, marks or buttons. The template candidate 710 can be read and edited from the external storage device 140 through the storage device 160 and a storage medium and can be further saved. Design data of the alignment mark can be inputted through the external storage device 140. The template candidate 710 matching with the feature points of an image on the screen of the display device 120 that is plotted by free hand through position display means such as a mouse pointer 730 can be read out from the storage device 160 on the basis of this image.

Figure 7:
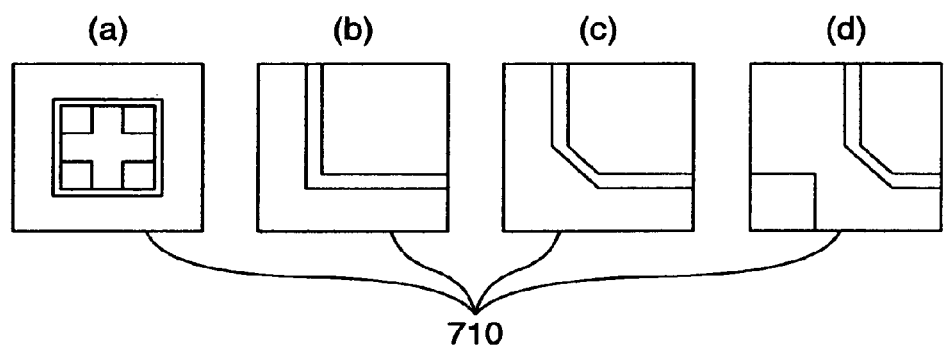
FIG. 7 is an explanatory view useful for explaining an example of the template candidate.
Figure 8:
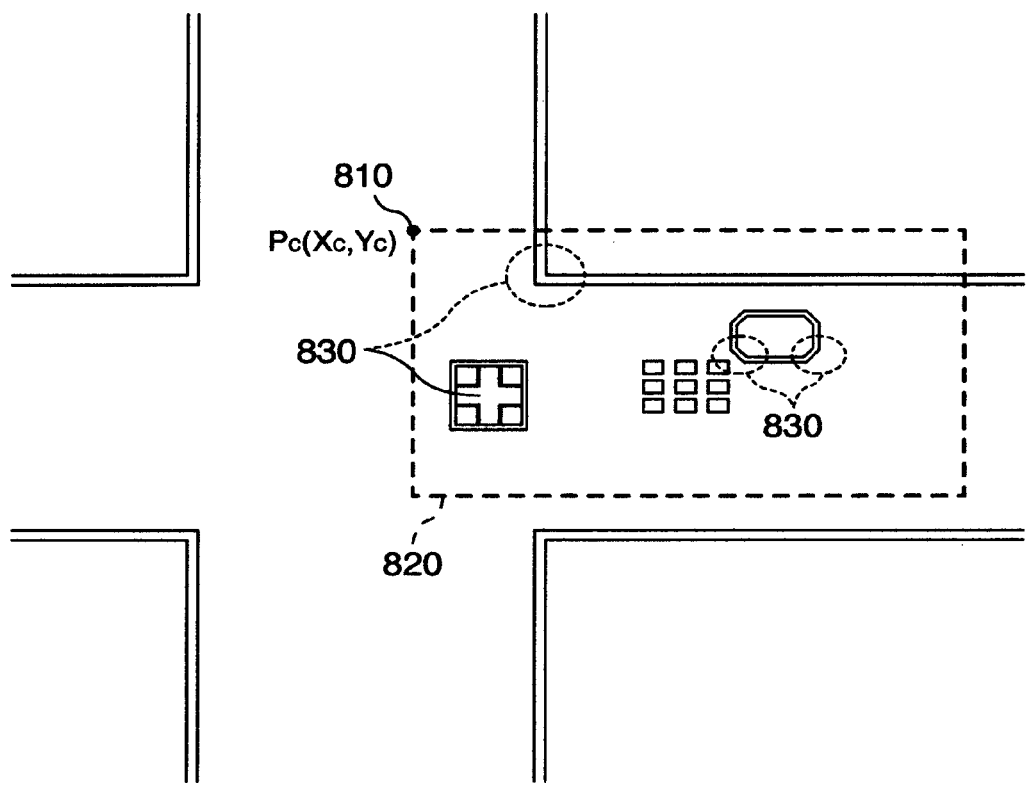
FIG. 8 is an explanatory view useful for explaining designated coordinates and a designation range for evaluating the template candidate.

FIG. 7 shows examples of the template candidate 710 used in this embodiment. The (a) of FIG. 7 shows an candidate formed by arranging a rectangle inside an outer profile of a rectangle and disposing a crisscross at the center. The (b) of FIG. 7 shows a candidate formed by juxtaposing an L-shaped figure with an outer L-shaped profile. The (c) of FIG. 7 shows a candidate formed by chamfering the corners of the pattern shown in the (b) of FIG. 7. The (d) of FIG. 7 shows a candidate formed by arranging a rectangle in the proximity of the pattern sown in the (c) of FIG. 7.

Figures shown in the (a) to (d) of FIG. 7 are formed by executing the program (S201) and are registered as the template candidates for searching the surface of the semiconductor wafer 1 to the storage device 160. When an alignment mark of the same kind existing on the semiconductor wafer 1 is searched, one ore more template candidates 710 are selected from the template candidates registered and are entered through the input device 110 (S202). The figures created and registered in the past can also be read out and used.

To improve matching accuracy, it is generally preferred that the template candidate has a large number of corners and the figure itself is independent. When the difference of the angle of the semiconductor wafer 1 is great or in the case of the wafer having a low contrast process, however, recognition defect may occur. For this reason, the template figure is preferably selected depending on the situation.

The transfer program is executed after the template candidate 710 is selected. The designated semiconductor wafer 1 taken out from the wafer cassette 11 of the load port 10 is transferred to the inspection unit 40 in the same way as in the first embodiment and is fixed onto the inspection stage chuck 42 (S203 to S205). Incidentally, it is also possible to select the template candidate 710 after the semiconductor wafer is fixed to the inspection stage chuck 42 and the operation can be switched by setting an inspection mode to the one that automatically executes only the inspection and evaluation process of the template candidate 710.

Figure 9:
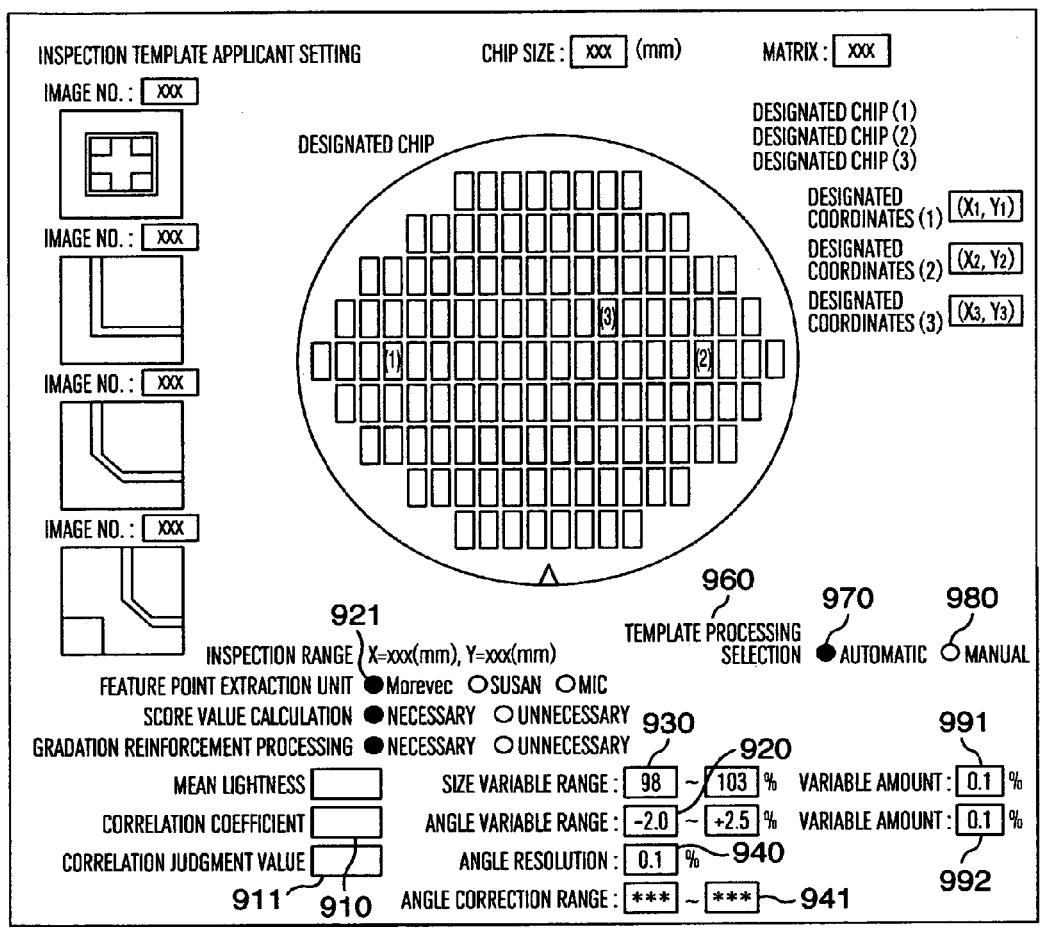
FIG. 9 is an explanatory view useful for explaining a set screen for evaluating the template candidate.

After the semiconductor wafer 1 is fixed onto the inspection stage chuck 42, the stage chuck 42 is moved to the template evaluation designated coordinates 810 designated in advance by driving the servo motor of the stage chuck 42 in the same way as in the first embodiment (S206). The template evaluation designated coordinates 810 are arranged as the screen for evaluating the template candidate 710 on the display device 120 as shown in FIG. 9 and one or more coordinates can be set through the input device 110. It is thus possible to set a plurality of coordinates and to determine a mean evaluation result of the template candidates 710.

The inspection stage chuck 42 is moved with the template evaluation designated coordinates 810 as the starting point and a pattern analogous to the template candidate 710 is searched from among the inspected patterns 830 formed inside the designated range 820 of the semiconductor wafer 1 by the CCD camera (S207).

The template candidate 710 registered to the storage device 160 is saved as the image data of line segments. The image of the inspected pattern 830 collected through the CCD camera (S208) is image processed into the image data subjected to line segmentation by the data processor 150 and pattern matching with the template candidate 710 entered is carried out, whenever necessary (S209). When the size is different between the template candidate 710 and the inspected pattern 830 or when an angle difference occurs in the semiconductor wafer 1, pattern matching accuracy drops. Therefore, pattern matching is carried out while the image data of the template candidate 710 is rendered variable (image correction unit) in the matrix shape within the designated range such as angle variable range setting 920 and size variable range 930 (shape correction setting unit) and in accordance with a size variable amount 991 and an angle variable amount 992 (variable amount setting unit). When a correlation coefficient 910 set in advance is satisfied in pattern matching, the position detector such as a laser scale built in the inspection stage 41 detects the coordinates of the inspected pattern 830.

The score value is calculated in accordance with equation (2), for example, on the basis of the feature points of the template candidate 710 and the feature points of the inspected pattern 830 subjected to pattern matching (S210). Calculation of the score value is not limited to this equation (2) but can be made by other means as long as they can numerically express and grade the degree of pattern matching. The feature points at the time of pattern matching are used as the feature points of the inspected pattern 830 and the feature points of the template candidate 710. However, it is possible to separately execute the image processing of the image data of each of them and to use the feature points extracted by the same or different feature point extracting unit. Analytical accuracy of the difference between the template candidate 710 and the inspected pattern 830 can be improved by changing pattern matching and the feature points used for calculating the score value.

[Expression 2]

$$S = \sqrt{\frac{Ms}{Ts}} \times \sqrt{\frac{Ms}{Td}} \times 10000 \quad (2)$$

Symbol S in equation (2) represents the size of the score value between the template candidate 710 and the inspected pattern 830 that are subjected to pattern matching. Symbol Ms represents the number of coincidence of the feature points between the inspected pattern 830 and the template candidate 710. Symbol Ts represents the total number of the feature points of the inspected pattern 830 collected and symbol Td represents the total number of the feature points of the template candidate 710.

The score value calculated is registered to the storage device 160 in association with the images of the template candidate 710 and the image of the inspected pattern 830 together with the angle correction value 1050 and the size correction value 1060 (correction value calculation unit) that are calculated on the basis of the size variable amount 991 and the angle variable amount 992 created by rendering the image of the template candidate 710 variable in pattern matching (S211). When the inspected pattern 830 is different from the template candidate 710 to be searched, the search inside the designated range 820 is continued. While the steps described above are repeated (S207 to S209), the inspected pattern 830 satisfying the correlation coefficient 910 is registered and the processing is continued until the search inside the designated range 820 is completed.

Pattern matching described above is executed by using geometric pattern matching, for example. The feature points of the image data are extracted by feature point extraction unit such as Moravec operator, SUSAN (Smallest Univalue Segment Assimilating Nucleus), MIC (Minimum Intensity Charge), or the like. The feature point extraction unit can be set by feature point extraction setting unit 921 such as the input space, icons or buttons provided on the template evaluation setting screen. Incidentally, it is also possible to execute pattern matching on the basis of the feature points by extracting the positional coordinates of the corners (corners of wiring pattern) of the inspected pattern 830 and the number of corners as the feature points from the segmented image data. The degree of coincidence of the feature points is different depending on the mode of the template candidate 710 to be searched and on the manufacturing process of the semiconductor wafer 1. It is therefore preferred to appropriately select an optimal method depending on the condition of use.

Figures 10, 11:
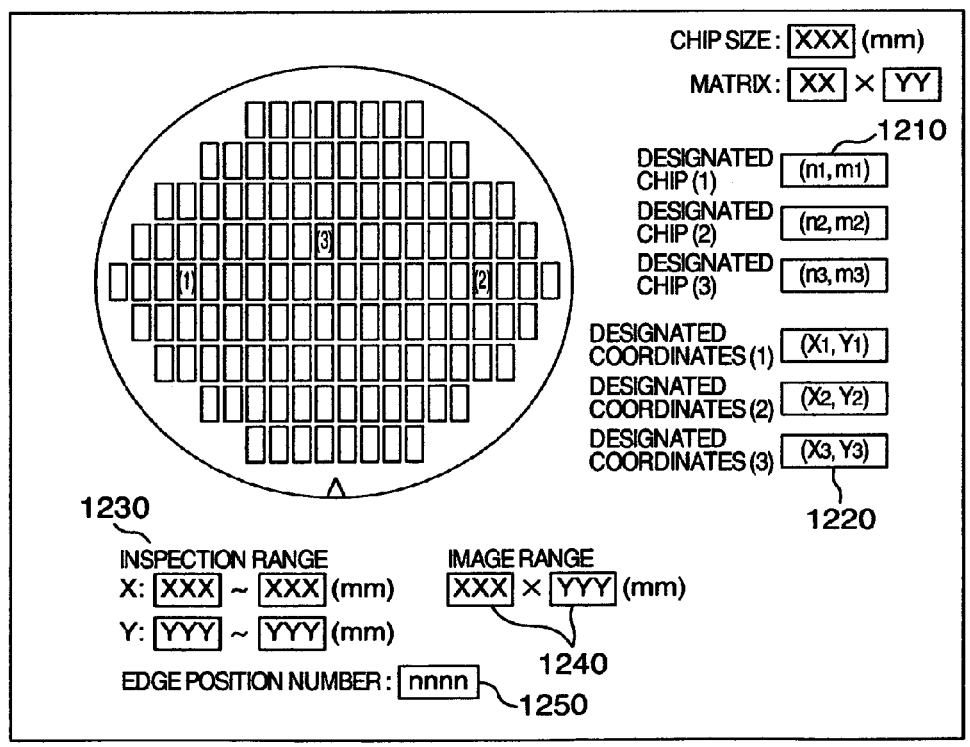
FIG. 10 is an explanatory view useful for explaining a screen that displays an evaluation result of the template candidate.
FIG. 11 is an explanatory view useful for explaining a set screen that inspects alignment marks formed inside a chip of a semiconductor wafer.

FIG. 10 shows a display screen showing the inspection result of the inspected pattern 830 detected from the template evaluation designated coordinates 810. The inspected pattern 830 satisfying the correlation coefficient 910 by pattern matching is displayed on the display device 1020 in a list form (analytical result display means) in association with various evaluation data such as a precedence 1010 of the score value, the image of the template candidate 710, the score value 1020, the acquired image 1030, the coordinates 1070, the judgment result 1040, the angle correction value 1050, the size correction value 1060, and so forth (S212). This display can be changed in the ascending or descending order of the score values 1020 by setting. When the template process selection unit 960 is automatic setting 970, the highest score value 1020 is automatically employed as the screen of the template. As the template candidate 710 that proves optimal is selected in this way on the basis of the analyzing means of the foreign matter inspection apparatus, the mismatching between human judgment and machine judgment can be suppressed and the optimal template can be selected. This selection of the template candidates 710 can also be set manually (manual setting 980), and the image that is believed appropriate can be selected as the template from the list display while looking up the acquired image 1030 and the score value 1020.

Next, the inspection stage chuck 42 is moved to the coordinates of the inspected pattern selected as the template (S213) and the angle of the inspection stage chuck 42 is changed for each angle resolution 940 (S214). The image position of the inspected pattern 830 is corrected (S215) and while the image data of the inspected pattern 830 is taken by the CCD camera for each angle (S216), the image data of the inspected pattern is registered as the template to the storage device 160 (S217). The processing is continued until imaging within the range set to the angle correction range 941 is completed (S214 to S218). After imaging of the image data group of the template for which angle correction degree is shifted is completed, the semiconductor wafer 1 is transferred from the inspection stage chuck 42 and is recovered into the wafer cassette 11 (S219). A plurality of template images the angles of which are made different from one another in advance is prepared and pattern matching is then executed by using the image data group the angles of which are shifted to improve identification accuracy of the patterns. The angle shift amount can be detected or anticipated from the image data of the image data group after pattern matching and θ correction can be made by pattern matching by using one alignment mark (first alignment mark 312 or second alignment mark 322) on the basis of the shift amount. Rough θ correction becomes possible when the angle difference of the semiconductor wafer 1 is great, and the correction speed as well as through-put of the correction processing can be improved.

In this embodiment, after the template candidate is selected as the template, the image data group generated by shifting the angle as the basic image data for angle correction is taken. However, it is also possible to execute this imaging process when the inspected pattern 830 is detected at the time of search inside the designated range 820 in pattern matching. In this way, the template search can be automated and the operation factor can be improved. To suppress the increase of the scale of the system as the image data collected increases, however, the image data group is preferably collected after the template is selected.

When the angle difference of the semiconductor wafer 1 is slight and the image data group and rough θ correction are not required or when the search processing speed of the template candidate 710 is of importance, the corresponding process steps can be skipped. Also, the data processing method can be changed through setting from the input device 110.

The edge position 440 is detected in the image data collected by the same method as that of the first embodiment and is likewise registered to the storage device 160. The image data and the edge position 440 are used as the template. After the template is evaluated, the semiconductor wafer 1 is recovered into the wafer cassette in the same way as in the first embodiment.

Embodiment 3

Next, a method for detecting the alignment marks formed on the semiconductor wafer 1 will be explained with primary reference to FIGS. 11, 12 and 16. However, the explanation of those portions which overlap with the first and second embodiments will be omitted and reference will be made also to FIGS. 1 and 2, whenever necessary.

Figure 16:
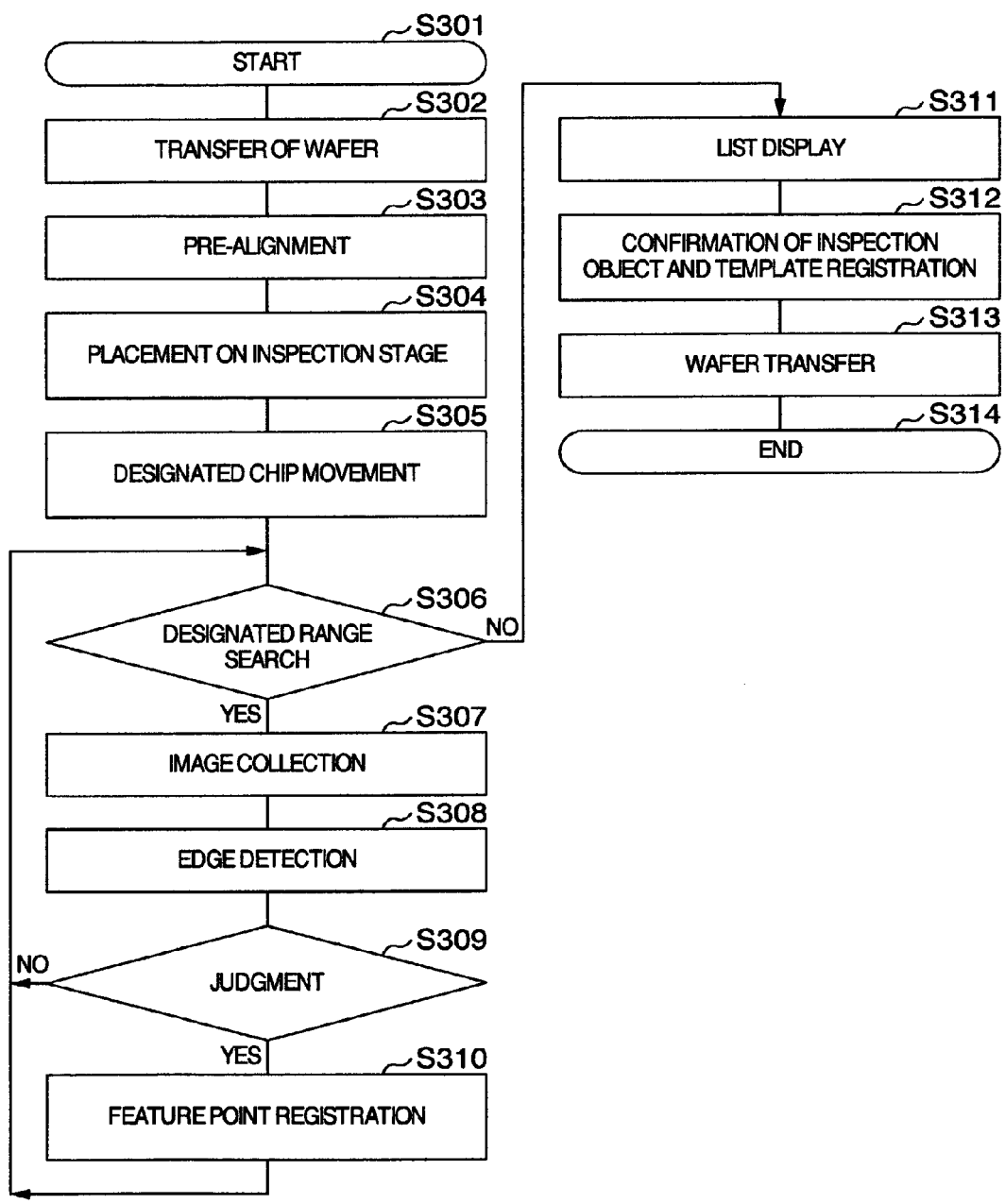
FIG. 16 is a flowchart that represents a method for inspecting a template candidate inside a semiconductor wafer.

FIG. 16 is a flowchart showing a processing procedure of the semiconductor wafer 1 in the third embodiment and FIG. 11 shows a set screen for detecting the alignment marks formed on the semiconductor wafer 1. The semiconductor wafer 1 as the measurement object is transferred by the wafer cassette 11 with the execution of the transfer program (S301) in the same way as in the first embodiment and is put on the inspection stage chuck 42 (S302 to S304). The inspection stage chuck 42 is then moved to the position of the designated chip 1210 in accordance with setting of the set screen (S305).

After positioning is made to the designated coordinates 1220 of the designated chip 1210, the inspection range 1230 is scanned by the CCD camera (S306), the mean density waveform is collected by the same method as that of the first embodiment while imaging is made, and the edge position 440 is detected (S307 to S308). When an inspection object satisfying the edge position number 1250 is detected in the image range 1240 set (S309), the inspection object is registered with the feature points such as the image data of the inspection object and its coordinates, the calculated edge number, and so forth, to the storage device 160 (S310). While the inside of the designated range 1220 is searched, the inspected object is registered (S306 to S310) and imaging is completed with completion of the designated range.

Figure 12:
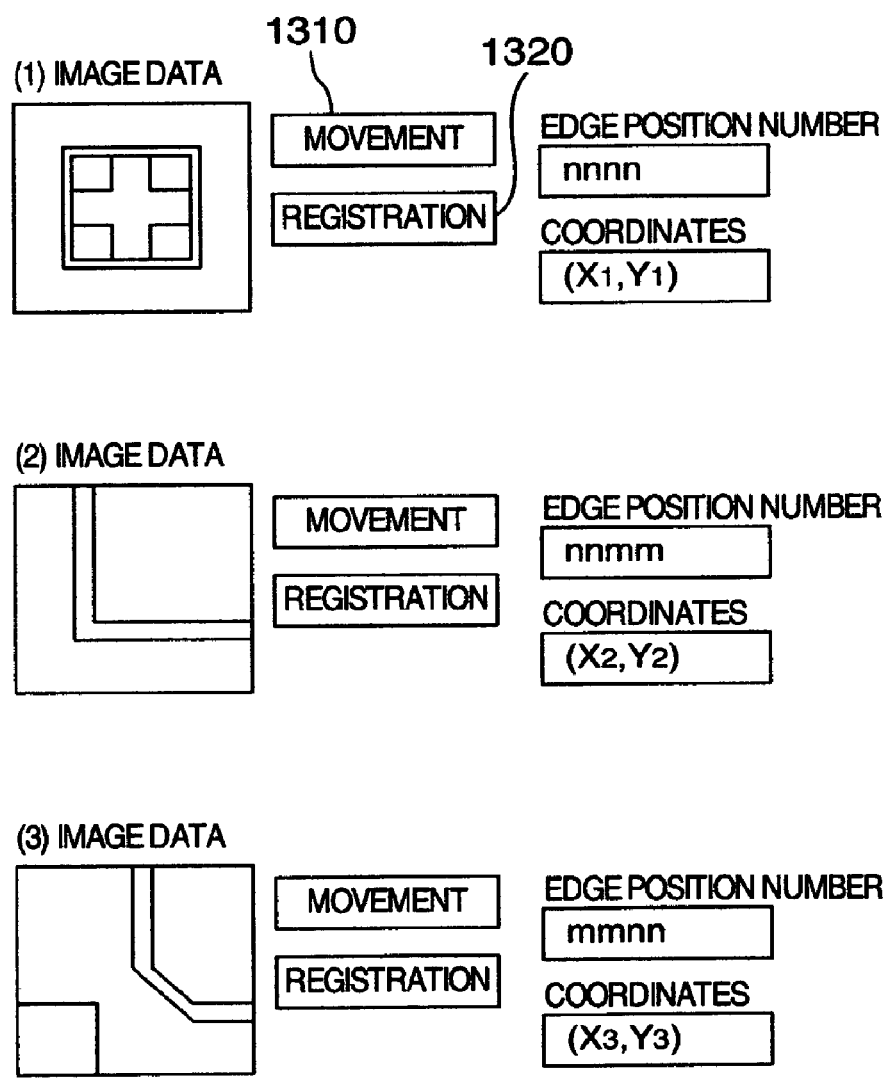
FIG. 12 is an explanatory view useful for explaining a screen that displays an inspection result of alignment marks formed inside a chip of a semiconductor wafer.

The registered image data is displayed in the list form either in an ascending order or a descending order of the numerical values of the edge position number 1250 on the display screen of the collected image of the inspection object in the display device 120 shown in FIG. 12 (S311). The image data of the inspection object displayed on the display device 120 is selected and the inspection stage chuck 42 is moved to the designated coordinates by selecting the buttons of movement indication unit 1310 through the input device 110 to confirm the inspection object with eye. Alternatively, the buttons of registration indication unit 1320 are selected to directly register the inspection object as the template (S312). When reliability is low, the image of the inspection object is collected in the same way as in the second embodiment and can be registered as the template. Incidentally, the buttons described above may well be input unit capable of inputting the signals and are not particularly limited. Therefore, input unit such as icons and keyboards can be employed.

Embodiment 4

Next, a template reliability evaluation method for evaluating reliability as to whether or not the selected template candidate 710 is effective as the template and whether or not other pattern formed on the semiconductor wafer 1 is mistaken as the template candidate will be explained with primary reference to FIGS. 13 and 17. The explanation of those portions which overlap with those, of the embodiments 1, 2 and 3 will be omitted and reference will be made also to FIGS. 1 and 2, whenever necessary.

Figure 13:
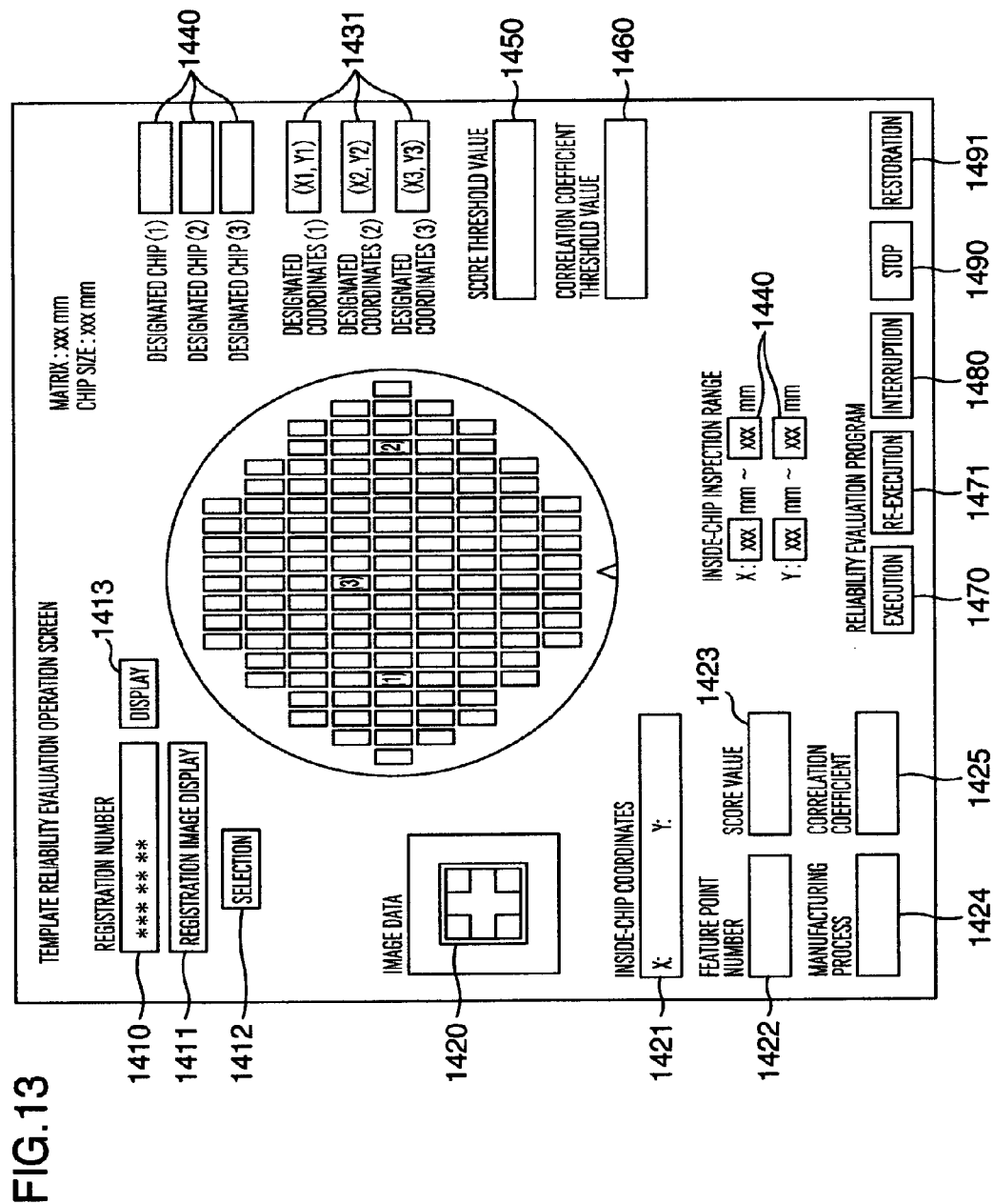
FIG. 13 is an explanatory view useful for explaining a set screen that evaluates reliability of the template candidate.
Figure 17:
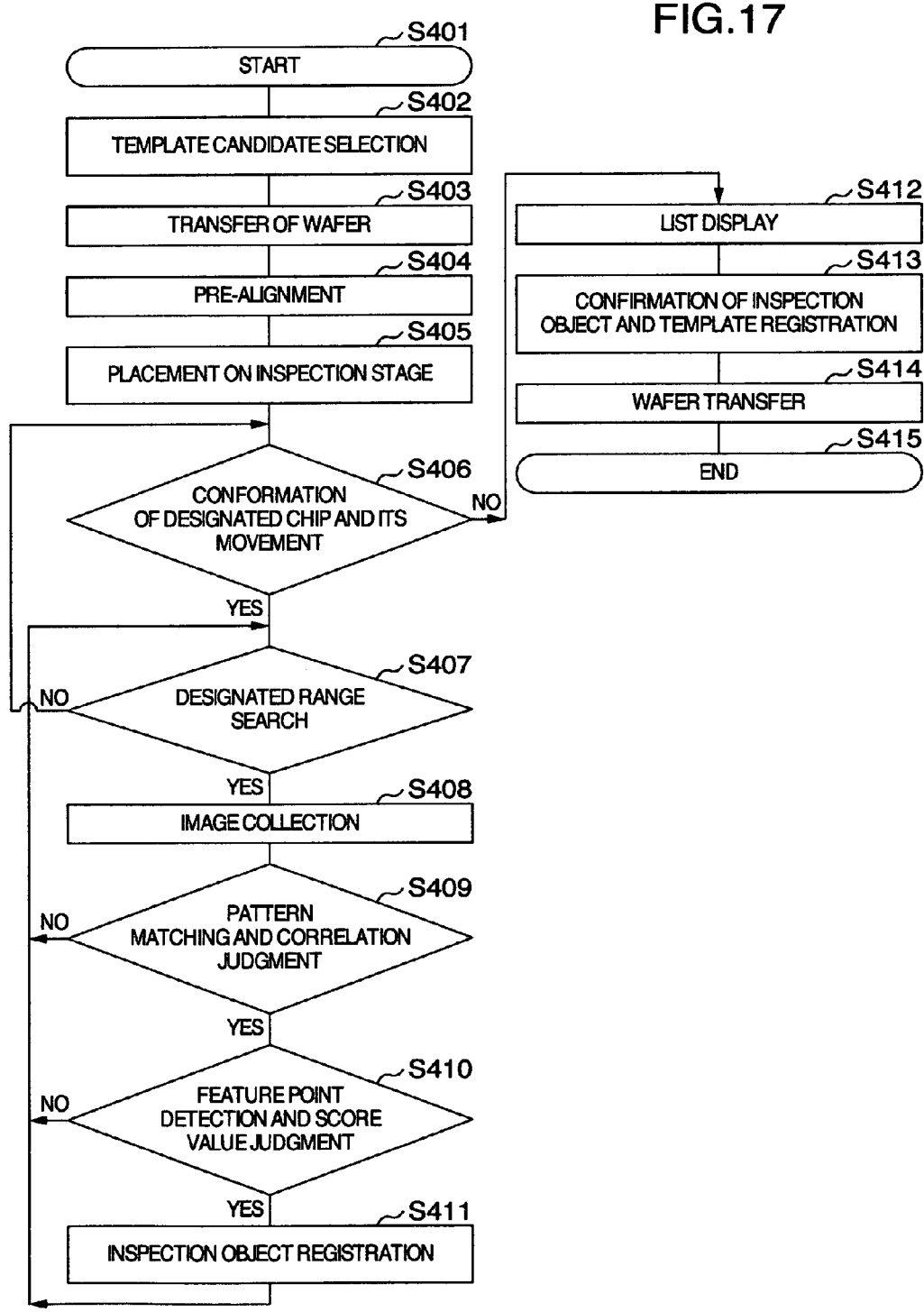
FIG. 17 is a flowchart that represents a method for evaluating reliability of the template candidate and for selecting an optimal template.

FIG. 13 shows an operation screen used for evaluating template reliability and FIG. 17 shows a flowchart of the processing procedure. The operation screen for template reliability evaluation shown in FIG. 13 includes registration number input unit 1410 for inputting the registration number of the template, display indication unit 1413 for displaying the image of the registration number, registration image display unit 1411 for executing collective thumbnail display of the template images, selection unit 1412 for deciding the template candidate 710 for which reliability evaluation is to be made, correlation coefficient setting unit 1460 for pattern matching, score threshold value setting unit 1450 for setting the threshold value of the score value, chip setting unit 1430 for designating the chip inside the semiconductor wafer to be inspected, coordinates setting unit 1431 for designating the coordinates inside the chip as the starting point, and inside-chip inspection range setting unit 1440 for setting the inspection range. The operation screen is constituted as a set screen on the display device 120 in such a fashion that the set value can be changed. The operation screen further has displaying functions by using image display unit 1420 for displaying the registration data of the template candidate 710 as the image at the time of registration, inside-chip coordinates display unit 1421 for displaying a relative position inside the chip, feature point number display unit 1422 for displaying the number of the feature points such as the edge, score value displaying unit 1423 for displaying the matching state of the feature points, correlation coefficient display unit 1425 for displaying the pattern matching state, and manufacturing process display unit 1424 for displaying a manufacturing process of the semiconductor wafer 1. As the reference data is displayed at the time of collection of the template candidate 710, the artificial setting mistake can be decreased and setting of the conditions for reliability evaluation becomes easy. Incidentally, though these input unit and display unit are constituted by buttons in this embodiment, other unit can be used as long as they can input and transmit the signals and can make display. Icons, keyboards and other signal input/transmitting unit and displaying unit may be used.

When the buttons disposed on the screen of the display device 120 are selected, the screen is displayed (S401). The group of the template candidates 710 stored in the storage device 160 is displayed in thumbnail display on the display screen (not shown) set separately. An arbitrary template candidate 710 is selected from the group of the template candidates 710 by candidate selection means (not shown) and the data of this template candidate 710 is read out from the storage device 160. When the registration number of the template candidate 710 is already known, it is possible to directly input the registration number by the input device 110 to the registration number input unit 1410, for example, to read the data by the display indication unit 1413 and to confirm the template candidate 710 by the image displaying unit 1420. Next, selection is made by the selection unit 1412 and the template candidate 710 is selected as the one for which reliability evaluation is to be made (S402). Incidentally, though reliability evaluation is made on the basis of one template candidate 710 in this embodiment, it is also possible to set two or more template candidates 710 and to simultaneously execute reliability evaluation. The evaluation time necessary for selecting the template can thus be shortened.

The semiconductor wafer 1 as the measurement object is transferred from the wafer cassette 11 by the same method as that of the first embodiment together with the execution indication unit 1470 of a reliability evaluation program and is put on the inspection stage chuck 42 (S403 to S405). The inspection stage chuck 42 is thereafter moved to the set position of the first chip setting unit 1430 in accordance with setting of the set screen (S406). Next, after the position is adjusted to the set position of the coordinates setting unit 1431 of the chip, the image data of the inspected object (pattern) formed on the semiconductor wafer 7 is collected (S408) while the set range of the inside-chip inspection range setting unit 1440 is scanned by the CCD camera (S407). Whether or not the predetermined value of the correlation coefficient threshold value setting unit 1460 is satisfied is judged while pattern matching is being executed (S409). The feature points are extracted by the edge detection shown in the first embodiment, etc from the inspected object (pattern) satisfying the predetermined correlation coefficient and the score value is calculated on the basis of the feature points (S410). The coordinates of the inspected object (pattern) satisfying the score value of the core threshold value setting unit 1450 are collected and are registered to the storage device 160 with the image data and the feature points such as the correlation coefficient and the score value (S411). Because the degree of pattern matching can be adjusted by the correlation coefficient threshold value setting unit 1460, the influences of contrast that changes in the manufacturing process can be suppressed. The number of the inspected objects (patterns) sampled can be controlled by the score threshold value setting unit 1450 and the extension of the inspection time can be suppressed. The inspected object (patterns) satisfying the condition are registered on occasion while the inside-chip inspection range 1440 is searched (S407 to S411) and the process is moved to the set position of the next chip setting unit 1430 with completion of scanning of the inside-chip inspection range 1440 (S406). Search of similar inspected object (patterns) is repeated and imaging is completed when the inspection of all the chips set by the chip setting unit 1430 is completed.

After all the chips set by the chip setting unit 1430 are inspected, the data of the object matters saved in the storage device 160 are displayed in the list form (not shown in the drawings) on the set screen disposed on the screen of the display device 120 (S412). This list is generated by associating the template candidate 710 with the image data of the inspected object (pattern) sampled and the feature points and are displayed in the ascending or descending order for each chip set by the chip setting unit 1430 on the basis of the numerical values representing the degree of similarity such as the score value and the correlation coefficient. Whether the candidate is suitable as the template can be judged from the score value and the numerical value of the correlation coefficient and the possibility of the recognition mistake can be judged from the sizes of the score values and the correlation coefficients between the inspected object (patterns) and the sizes of the correlation coefficients. Stability of pattern matching can be judged from the order of the inspected object (patterns) and the difference of the numerical values among the chips set by the chip setting unit 1430. The template candidate 710 is selected by referring to the result of the list and the template selection unit (not shown) arranged on the screen of the display device 120 is selected. The candidate is thus registered as the template (S413).

Incidentally, when a plurality of template candidates is evaluated, the data processing unit 50 judges and adopts a suitable template candidate 710 from the relation described above by selecting the automatic selection unit. However, it is also possible to confirm the condition of the list display by employing manual setting and to select the template candidate 710. When this manual setting is employed, reliability can be re-evaluated by selecting the re-execution indication unit 1471 by changing various kinds of setting when the evaluation result of the list display is not satisfactory, for example. When various kinds of setting are not changed, in particular, re-evaluation can be of course made. Because this evaluation can compare and evaluate a plurality of template candidates 710 under the same condition such as the θ angle error of the semiconductor wafer 1, for example, the evaluation method is effective for shortening the evaluation time and selecting a template having high reliability. However, the template registration step (S413) is not indispensable and may be skipped when only reliability evaluation of the template candidates is made. The wafer is transferred with completion of the evaluation by the same method as that of the first embodiment and is recovered into the original wafer cassette 11, and the program is completed (S414 to S415). Reliability and operation factor of the foreign matter inspection apparatus can be drastically improved because selection of the template candidates 710 and the set value of the threshold value for avoiding the possibility of the recognition mistake of the inspected object and the recognition mistake itself can be confirmed in advance owing to this reliability evaluation function.

When the reliability evaluation program gets frozen due to the recognition mistake during evaluation, the evaluation can be interrupted or stopped by using the interruption indication unit 1480 or the stop indication unit 1490. Furthermore, the inspection apparatus can be restored to the initial state by releasing the error by selecting the restoration unit 1491.

Embodiment 5

Figure 18:
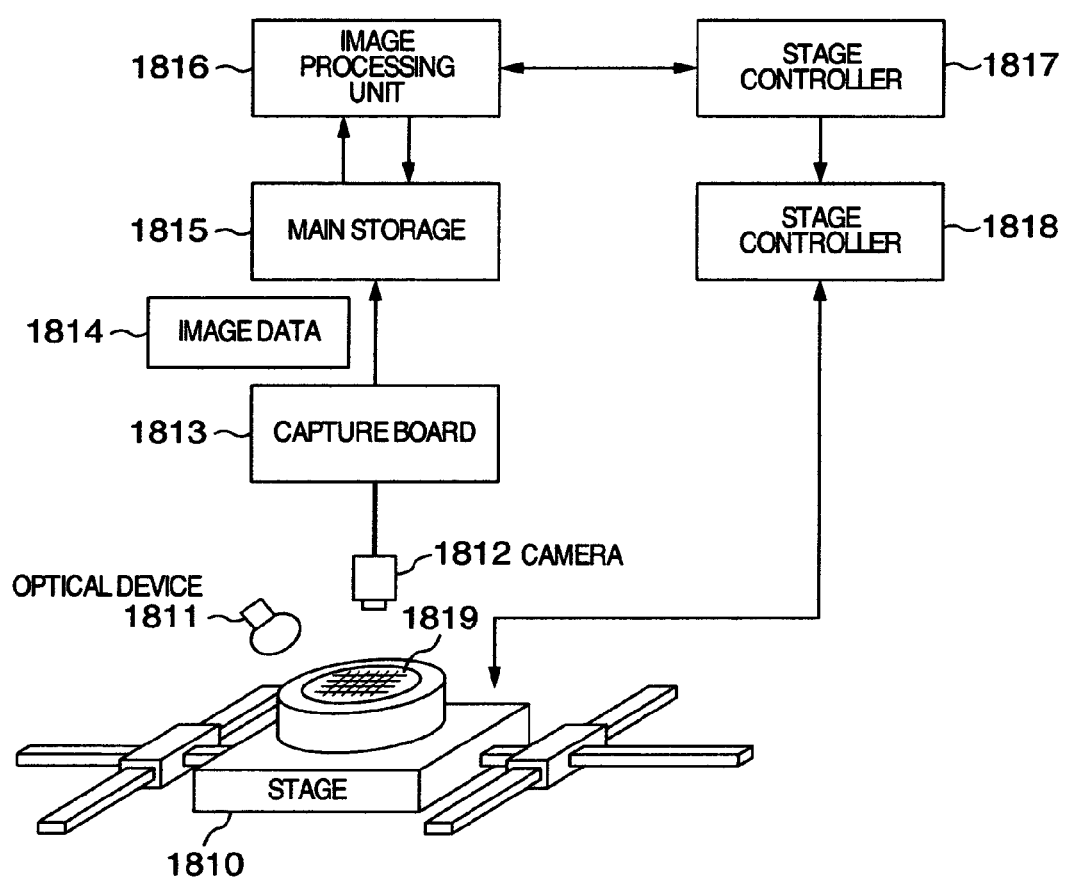
FIG. 18 is a structural view of an inspection apparatus according to an embodiment of the invention.

An inspection apparatus for an inspected object according to still another embodiment of the invention will be explained. FIG. 18 shows a construction of the inspection apparatus in this embodiment. In the drawing, reference numeral 1810 denotes a stage for moving and rotating a wafer 1819. Reference numeral 1811 denotes an optical device for irradiating the surface of the wafer 1819. Reference numeral 1812 denotes a camera for imaging the surface of the wafer 1819 irradiated by the optical device 1811. Reference numeral 1813 denotes a capture board for storing the surface image of the wafer 1819 taken by the camera 1812. Reference numeral 1814 denotes image data stored by the capture board 1813. Reference numeral 1815 denotes a main storage for subjecting the image data 1814 to processing. Reference numeral 1816 denotes an image processor for processing the image data 1814. Reference numeral 1817 denotes a storage controller having stage controlling software for controlling the stage 1810. Reference numeral 1818 denotes a stage controller for controlling the stage 1810. Reference numeral 1819 constitutes software.

Figure 19:
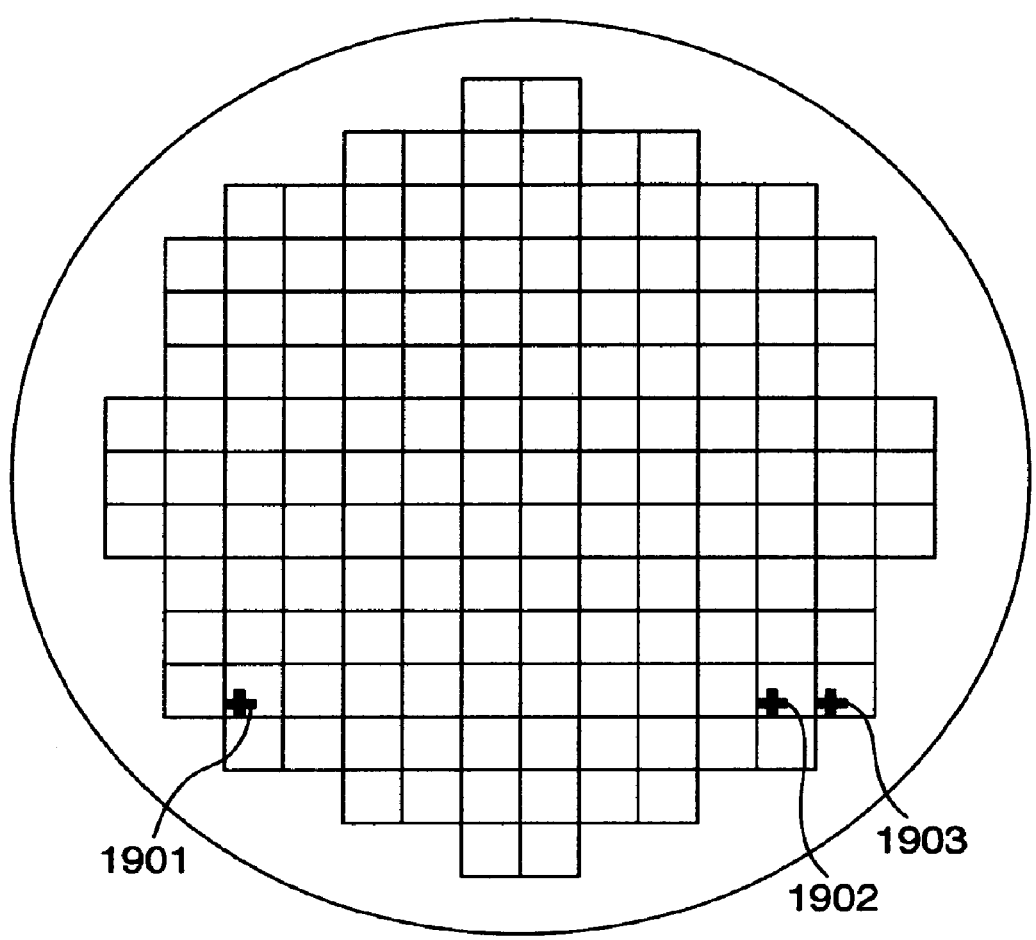
FIG. 19 shows correction marks on a wafer by alignment.

FIG. 19 shows an arrangement of correction marks formed on the wafer 1819 according to this embodiment. Reference numerals 1901 and 1902 denote correction marks, respectively, and reference numeral 1903 denotes a confirmation mark. The confirmation mark may exist at any position as long as it exists in the proximity of the correction mark 1902.

Figure 20:
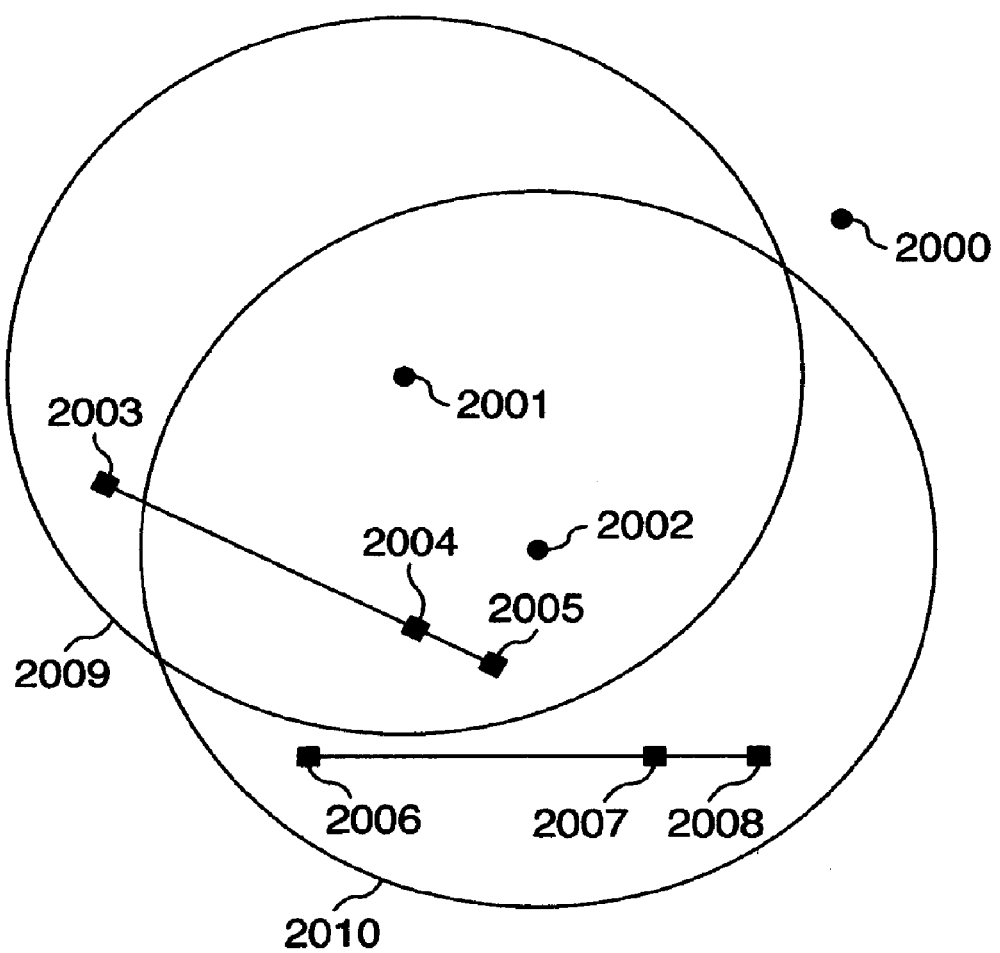
FIG. 20 shows the wafer and movement of the correction marks by alignment.

FIG. 20 shows an orbit of the wafer 1819 from its transfer to the stage 1810 to its positioning. Reference numeral 2009 denotes the position of the wafer 1819 immediately after it is transferred to the stage 1810. Reference numeral 2000 denotes the center of revolution of the stage 1810. Reference numeral 2001 denotes the center of the wafer when the wafer 1819 exists at the position 2009. Reference numerals 2003, 2004 and 2005 denote coordinate positions of the correction marks 1, 2 and 3, respectively, when the wafer centers 2003, 2004 and 2005 exist at the position 2009. Reference numeral 2010 denotes the position of the wafer 1819 after positioning is made. Reference numerals 2006, 2007, 2008 and 2009 denote the coordinate positions of the correction marks 1, 2 and 3, respectively, when the wafer 1819 exists at a position 2100.

Figure 21:
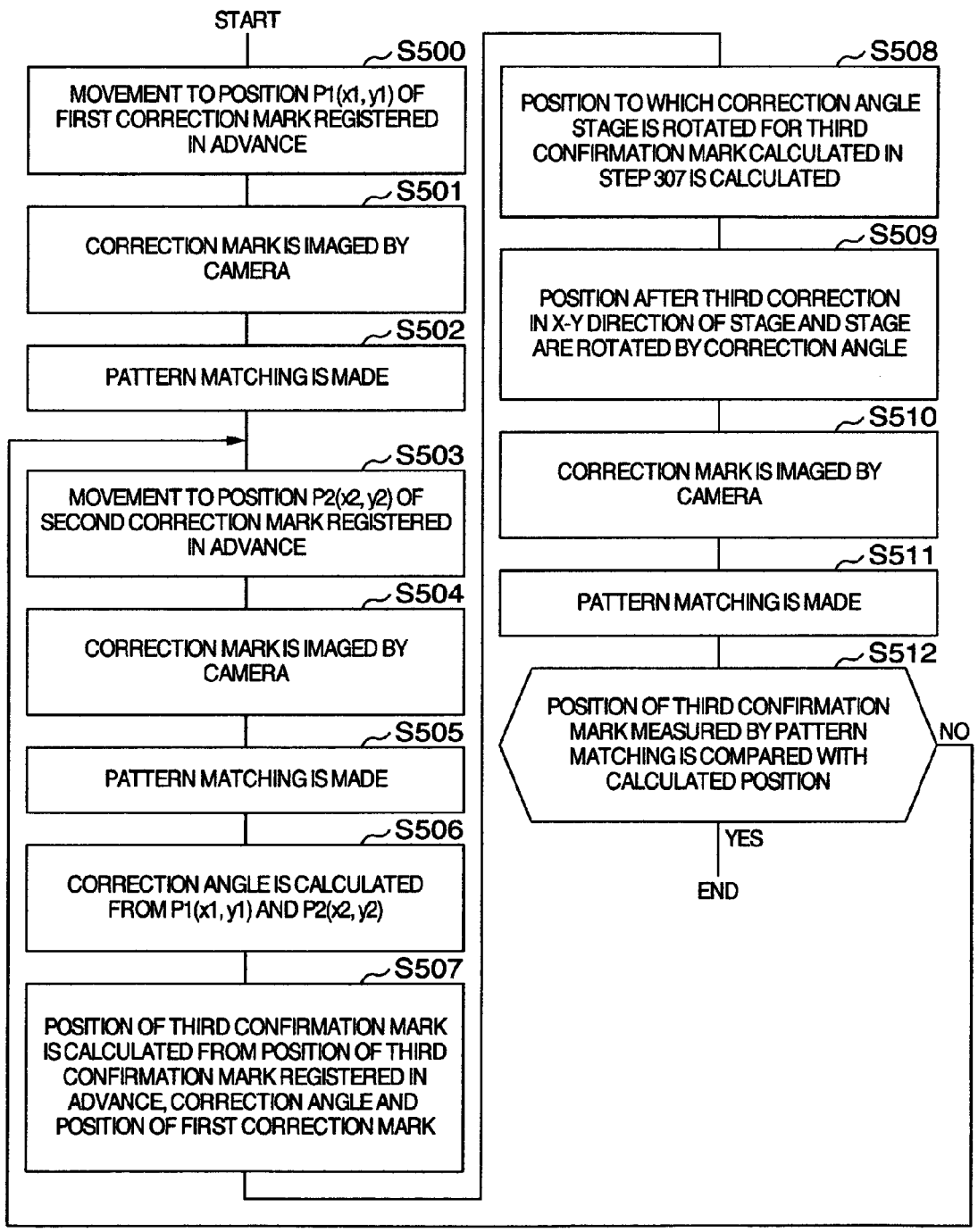
FIG. 21 is a processing flowchart showing an execution method of alignment.

FIG. 21 shows the flow of an alignment process in this inspection apparatus.

In step S500, the stage 1810 is moved to a coordinate position P1(x1, y1) of the correction mark 1901 registered in advance. The correction mark 1901 is imaged by the camera 1812 in step S501. Pattern matching is executed for the image taken in step S502 and the coordinate position of the correction mark 2003 is detected. At this time, the wafer 1819 exists at the position 2009 while it is transferred by the stage 1810 and the correction mark 1 exists at the coordinate position 2003. After the coordinate position of 2003 detected is acquired in step S502, the stage 1810 is moved to the coordinate position of the correction mark 2 registered in advance in step S503. At this time, the wafer 1819 exists at the position 2009 while transferred by the stage 1810 and the correction mark 2 exists at the coordinate position 2004. The image of the correction mark 2 is taken by the camera 1812 in step S504. Pattern matching is executed for the image taken in step S505 and the coordinate position of the correction mark 2 is detected. A correction angle is calculated in step S506 from the coordinate positions 2003 and 2004 of the correction marks 1 and 2 detected in step S502 and S505. The third coordinates before position correction is made are determined in step S507 from the correction angle calculated in S506, from the coordinates of the first correction mark calculated in step S502 and from the coordinates of the third confirmation mark registered in advance. In step S508, the coordinate position when the stage 1810 is rotated to the correction angle is calculated with respect to the coordinates of the third confirmation mark calculated in step S507. In step S509, the stage 1810 is rotated by the correction angle calculated in step S506 and is moved to the coordinate position calculated in step S509. Imaging of the confirmation mark 3 is executed by the camera 1812 in step S510. The coordinates 2008 of the confirmation mark 3 are detected by pattern matching in step S511. In step S512, the difference is calculated between the coordinate position 2008 of the correction mark 3 calculated in step S508 and the coordinate position 2008 of the correction mark 3 measured in step S511. Position correction is completed when the difference value is within a threshold value that is registered in advance. When the difference value is greater than the threshold value, the process steps from S503 are repeated. The embodiments of the invention are not particularly limited to those described above but can be changed or modified in various ways within the scope of the invention.

Although the invention has thus been explained about the foreign matter inspection apparatus for the manufacture of semiconductor integrated circuits by way of example, the alignment technology according to the invention can be widely applied to various process steps and apparatuses necessary for producing disks, flat panel display devices, masks, and so forth, produced from flat panels such as substrates of flat panel display devices glass substrates of TFT and ALTIC substrates.

Although the invention has been explained about the embodiments of the foreign matter inspection apparatus, the invention can be similarly applied to semiconductor inspection apparatuses and semiconductor manufacturing apparatuses without particular limitation. For example, the invention can be applied to measuring apparatuses and exposure apparatuses such as CD-SEM as long as they can execute position correction processing of inspected objects by using alignment marks formed on the inspected objects.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection apparatus for inspecting an object comprising:
   an imaging system configured to acquire a plurality of alignment mark images from the object;
   a computer implementation system configured to draw a plurality of template candidate images having different shapes; and
   a processing system configured to use a function to calculate a score based on a correlation between said alignment mark images and said template candidate images, wherein:
   said processing system is configured to acquire a first feature point from at least one of the first alignment mark images and a second feature point from at least one of the template candidate images, and said function is expressed by a number of matched feature points between said first feature point and said second feature point, a number of first feature points, and a number of second feature points.

2. The inspection apparatus according to claim 1, wherein said processing system is configured to normalize at least one of the alignment mark images.

3. The inspection apparatus according to claim 1, wherein said processing system is configured to differentiate at least one of the alignment mark images.

4. The inspection apparatus according to claim 3, wherein said processing system is configured to change brightness of the at least one differentiated alignment mark image.

5. The inspection apparatus according to claim 1, wherein said computer implementation system includes a computer aided design system.

6. The inspection apparatus according to claim 1, further comprising:
a storage system configured to store design data of at least one of the alignment mark images,
wherein said design data is input to said computer implement system.

7. The inspection apparatus according to claim 1, wherein said computer implementation system is configured to acquire a figure of at least one template candidate image by using at least one of a solid line, a dash line, a chain line, a circle and a rectangle.

8. The inspection apparatus according to claim 1, wherein said processing system changes at least one of: a size of at least one template candidate image, and an angle of at least one template candidate image.

9. The inspection apparatus according to claim 8, wherein said processing system executes a pattern matching between the at least one alignment mark image and template candidate image by changing at least one of said size and said angle.

10. The inspection apparatus according to claim 1, further comprising:
a storage system configured to store at least one template candidate image.

11. The inspection apparatus according to claim 1, further comprising:
a stage system configured to mount said object, wherein:
said processing system acquires misalignment information between a center of said stage system and a center of said object, and
said processing system changes position of said object by using said misalignment information.

12. A method of aligning a position of an object, the method comprising steps of:
acquiring by way of an imaging system, a plurality of alignment mark images from the object;
drawing, by way of a computer implementation system, a plurality of template candidate images having different shapes;
calculating, by way of a processing system using a function, a score based on a correlation between said alignment mark images and said template candidate images; and
acquiring a first feature point from at least one of the first alignment mark images and a second feature point from at least one of the template candidate images,
wherein said function is expressed by a number of matched feature points between said first feature point and said second feature point, a number of first feature points, and a number of second feature points.

13. The inspection method according to claim 12, further comprising the step of normalizing at least one of the alignment mark images.

14. The inspection method according to claim 12, further comprising the step of differentiating said at least one of the alignment mark images.

15. The inspection method according to claim 14, further comprising the step of changing brightness of the at least one differentiated alignment mark image.

16. The inspection method according to claim 12, wherein said computer implementation system includes a computer aided design system.

17. The inspection method according to claim 12, further comprising the step of:
storing design data in a storage system for at least one of said alignment marks,
wherein said design data is input to said computer implementation system.

18. The inspection method according to claim 12, further comprising the step of:
acquiring, by way of the computer implementation system, a figure for at least one template candidate image by using at least one of a solid line, a dash line, a chain line, a circle and a rectangle.

19. The inspection method according to claim 12, further comprising the step of:
changing, by way of the processing system, at least one of a size of at least one template candidate image, and an angle of at least one template candidate image.

20. The inspection method according to claim 19, further comprising the step of:
executing, by way of the processing system, a pattern matching between the at least one alignment mark image and said template candidate image by changing at least one of said size and said angle.

21. The inspection method according to claim 12, further comprising the step of:
storing at least one template candidate image in a storage system.

22. The inspection method according to claim 12, further comprising the step of:
mounting the object on a stage system, wherein:
said processing system acquires misalignment information between center of said stage system and center of said object, and
said processing system changes position of said object by using said misalignment information.

* * * * *